United States Patent [19]

Claude

[11] 4,297,104
[45] Oct. 27, 1981

[54] METHOD OF DETECTING OR IDENTIFYING VIRUS ANTIGENS, ERYTHROCYTE OR CELL ANTIGENS OR ANTIBODIES IN A BIOLOGICAL MEDIUM

[75] Inventor: Matte Claude, Paris, France
[73] Assignee: Centre National de Transfusion Sanguine, France
[21] Appl. No.: 14,547
[22] Filed: Feb. 23, 1979
[30] Foreign Application Priority Data
   Feb. 28, 1978 [FR] France .................. 78 05758
[51] Int. Cl.³ .............. G01N 33/54; G01N 33/80
[52] U.S. Cl. ................ 23/230 B; 422/72; 424/11; 424/12
[58] Field of Search ........... 422/72; 23/230 B; 424/12, 11

[56] References Cited

U.S. PATENT DOCUMENTS 4,148,607  4/1979  Bernoco .................... 422/72

FOREIGN PATENT DOCUMENTS 940428   1/1974  Canada .
7506162  5/1975  Netherlands .
7709530  8/1977  Netherlands .
1185228  3/1970  United Kingdom .
1212414 11/1970  United Kingdom .
1337425 11/1973  United Kingdom .

OTHER PUBLICATIONS

"Gradwohl's Clinical Laboratory Methods and Diagnosis", vol. I., S. Frankel et al. eds., 756–757, 302–304, C.V. Mosby Co., Saint Louis, 1970.
N. Henning, "Klinische Laboratoriums Diagnostik," third edition, pp. 302 to 304, 1966.

Primary Examiner—Sidney Marantz
Attorney, Agent, or Firm—Larson and Taylor

[57] ABSTRACT

A method for detecting or identifying virus antigens or erythrocyte or cell antigens or antibodies in a biological medium. The reaction of analysis is conducted in a vessel the wall of which has a point of convegence or apex situated on the axis of symmetry of the vessel; the wall of said vessel is coated by molecules with antigenic or antibody activity chosen with respect to the antigen or the antibody to detected; the reaction medium comprising cells or particles and a serum is introduced into the vessel and subjected to a centrifugal force substantially parallel to the aforementioned axis under conditions such that in a first period all the cells or particles, whether they characterize a reaction with a positive result or a negative result, progressively stick to and remain stuck to the wall of the vessel, and then, in a second period, only the cells or particles characterizing one kind of reaction remain stuck to the wall of the vessel by means of said molecules coating said vessel wall, whereas the cells or particles characterizing the other kind of reaction are collected at the apex of the vessel.

33 Claims, 26 Drawing Figures

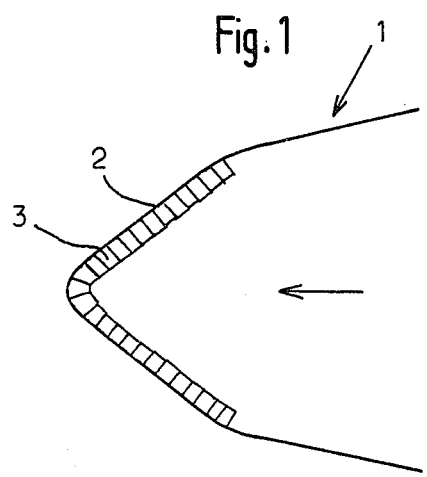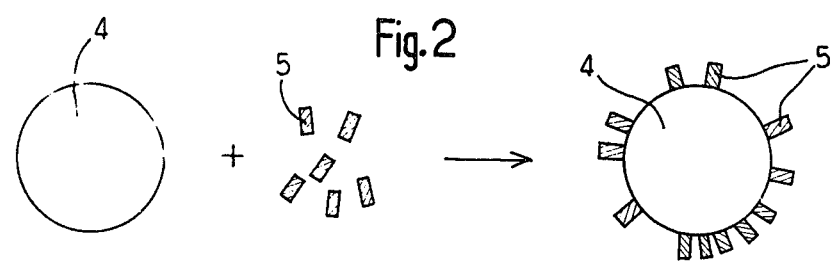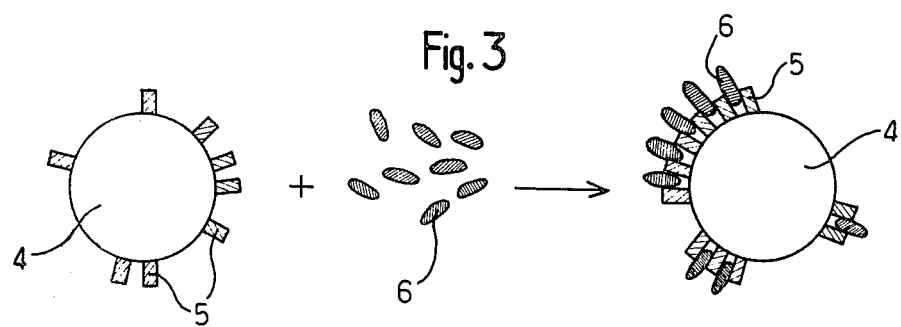

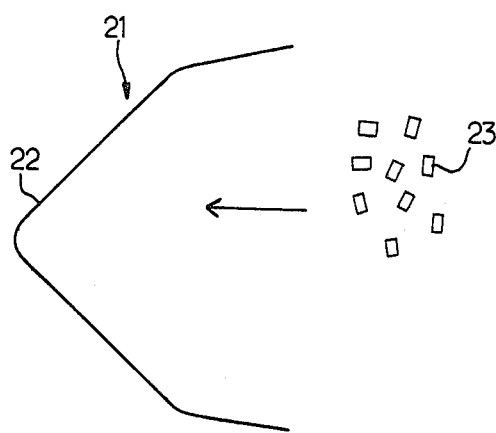
Fig.11
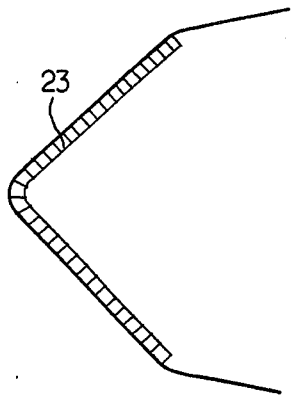
Fig.12
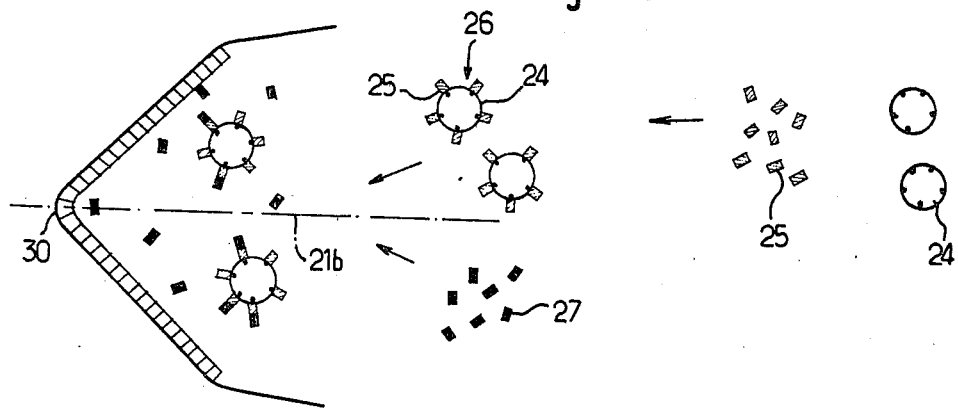
Fig.13a
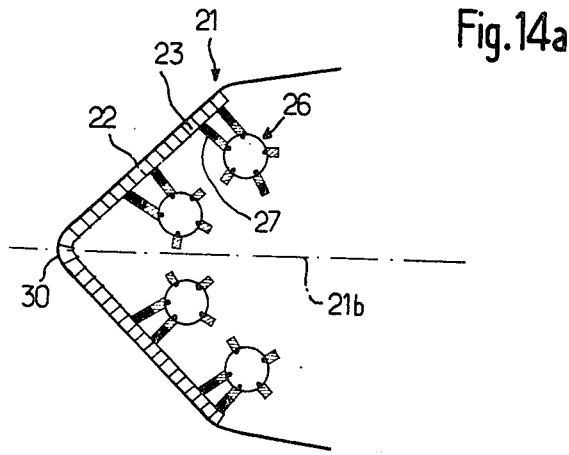
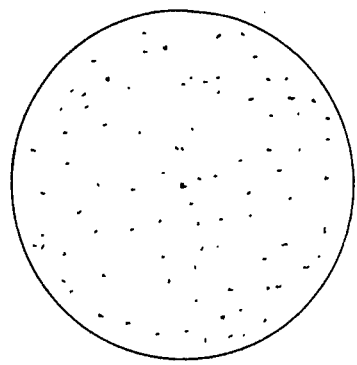
Fig.14a

METHOD OF DETECTING OR IDENTIFYING VIRUS ANTIGENS, ERYTHROCYTE OR CELL ANTIGENS OR ANTIBODIES IN A BIOLOGICAL MEDIUM

BACKGROUND OF THE INVENTION

1. Field of the Invention

The invention relates to a method of analysing a liquid biological medium such as human blood in order to detect or identify viruses therein having antigen properties (i.e. virus antigens) or erythrocyte or cell antigens or antibodies.

In medical analysis, a frequent problem is the exact determination of the nature of the antigens carried by a cell or particle, and the nature of the antibodies or virus antigens in a serological medium. This applies inter alia to blood transfusions, where it is essential to ensure that the blood of the donor or donors is compatible with the blood of the future recipient.

Any incompatibility between the two blood systems is because the plasma of one blood system may contain molecules called "antibodies" which may become fixed on to complementary structural units or "antigen units" or "antigens" in the membranes of the red corpuscles or erythrocytes in the other blood system. An antigen of this kind is called an "erythrocyte antigen". An antibody capable of becoming fixed only on to a particular antigen is called an antibody "specific" to the antigen. Antibodies, if fixed on to antigen units carried by erythrocytes, may agglutinate them and destroy or seriously injure them, and may thus produce accidental illness during blood transfusions.

It is also essential to ensure that the donor's blood cannot transmit to the recipient certain diseases which are identified by detecting a virus antigen (i.e. a virus having antigenic properties) or an antibody specifically corresponding to the disease. One such disease is post-transfusion hepatitis, which may occur in the recipient if the donor's blood contains a virus called HB virus, which carries the $HB_s$ antigen.

This clearly shows the great importance of examining the blood of donors and recipients to detect any kinds of antibodies, cellular antigens or viruses having antigenic properties (i.e. virus antigens) which are capable of producing incompatibility reactions or disease in the recipients.

To make a transfusion, therefore, it is essential to be protected from any lack of sensitivity of the detection method. In addition, there should be practically no risk of error in determining the specificity of erythrocyte or cell antigens, antibodies or viruses (or virus antigens).

For the sake of clarity, we shall define certain terms used in the following description.

"Virus having antigenic properties" means a virus which reacts with a known specific antibody. Hereinafter this will be denoted by "virus having antigenic properties" or more briefly, "virus" or "virus antigen".

"Immunoglobulins" will refer to protein molecules from an animal species and having either a simple antigen activity or a simple antibody activity or both activities simultaneously, i.e. antigenic and antibody. In the case of each animal species, both man and other animals (such as the goat, guinea-pig or rabbit), immunoglobulins belong to various immunochemical classes, i.e. immunoglobulins in a class called A—called IgA for short—, immunoglobulins in a class G (called IgG), etc. In general, an immunoglobulin in the immunochemical class X and from the animal species I will be denoted IgX I.

The term "test serum" used here denotes a serum (or solution) containing immunoglobulins from a certain species of animals and in a certain immunochemical class, e.g. class G human immunoglobulins (IgG) having a specific antibody activity towards a particular erythrocyte or cell antigen in a group of individuals from the same species, i.e. a group of human beings in the present example. We prefer here to speak of a group of individuals since, as any serologist knows, a single erythrocyte or cell antigen is not necessarily present in all individuals of a given species of animals but is usually present in only some individuals, which form a group.

Similarly the terms "test corpuscles", "test cells" or "test particles" refer to corpuscles, cells or particles having antigen units from a certain species of animals which may become fixed to immunogloubulins carrying the antibody unit corresponding specifically to the antigen units.

"Antiglobulin" denotes an immune serum from an animal species II different from a species I and supplying immunoglobulins having a specific antibody activity towards IgX I. The antiglobulin will be called Ig II anti-IgX I, or simply anti-IgX I if no confusion is possible.

2. The Prior Art

It is known to use "Coombs" reactions for determining the presence of antibodies (or erythrocyte antigens) in the plasma or serum of blood (or in erythrocytes). The known method is as follows, e.g. when determining whether the plasma of a sample of human blood contains a particular antibody, e.g. a specific anti-D antibody, or in other words contains immunoglobulins specific to the "D" antigen, some of which are in the immunochemical class G and will therefore be called "IgG". The plasma to be analysed is incubated in a tube with erythrocytes carrying D antigen units, i.e. erythrocytes having an antigen activity specific to the antibody for which a search is being made. Any immunoglobulins of the specific antibody present in the plasma will become fixed, during the contact period, on to the corresponding antigen units on the corpuscles. The resulting reaction medium is washed and then incubated with an antiglobulin, e.g. a goat serum providing anti-human IgG immunoglobulins. During the incubation, a goat immunoglobulin supplied by the antiglobulin, owing to its specific anti-human unit becomes fixed to any human immunoglobulin which has become fixed to an antigen unit specific to an erythrocyte. After the incubation, the reaction medium is centrifuged; if the specific anti-D antibody searched for was actually present in the plasma, this results in agglutination of the erythrocytes produced by the immunoglobulins provided by the antiglobulin, as a result of the production of the following chains of bonds:

Erythrocyte (D antigen)/specific anti-D human immunoglobulin/anti human-immunoglobulins/specific anti-D human immunoglobulin/(D antigen) erythrocyte. The agglutination occurs in the form of a deposit of agglutinated erythrocytes at the bottom of the tube, but the deposit is not always easy to distinguish from a deposit of non-agglutinated erythrocytes. The two deposits are distinguished by gently agitating the tube contents. In negative reactions, i.e. reactions brought about on the plasma of blood not containing the specific anti-D antibody, the non-agglutinated erythrocytes return to homogeneous suspension, whereas in positive reactions the erythrocytes continue to stick together in relatively large groups.

This method involves relatively long, complicated reactions, and sometimes these reactions lack sensitivity, which may be dangerous.

The problem of exactly determining the nature of the antigens carried by a cell also occurs when transplanting organs. It is known that lymphocytes carry a certain number of antigens called "HLA"-system antigens. Before any surgical transplantation, it is essential to determine which HLA antigens are carried by the donor's and recipient's lymphocytes, in order to ensure that there is at least theoretical histo-compatibility between the lymphocytes from these two different individuals, since otherwise it will be impossible to transplant an organ. Owing to the large number of different HLA-system antigens which may be carried by lymphocytes, a large number of elementary reactions (e.g. 100) have to be carried out to determine the specific nature of the HLA antigens present. These operations are all the more difficult in that lymphocyte cells are available only in very small quantities and can thus be used only in microreactions.

Nowadays some viruses or virus antigens (e.g. $HB_s$ antigen) are detected by radio-immunological methods which are very expensive and cause pollution and therefore require special authorization.

SUMMARY OF THE INVENTION

An object of the invention is to provide a method of analysing a biological medium, e.g. a human blood sample, for detecting or identifying virus antigens, erythrocyte or cell antigens or antibodies in the medium, the method being of general use and suitable for detecting any kind of virus antigen in a liquid biological medium and any kind of erythrocyte or cell antigen or antibody in a blood sample.

Another object of the invention is to provide a method of the aforementioned kind for highly sensitive analysis, the method being much better than the known methods but very highly specific with regard to the virus antigen, the erythrocyte or cell antigen or the antibody for which a search is being made. By convention, a method of analysis is said to be sensitive in proportion to the smallness of the amount which it can detect of a virus antigen, an erythrocyte or cell antigen or a specific antibody, and the method is more specific in proportion as it can detect all the various specific antigens or antibodies without error, i.e. without confusing them. In other words, a virus antigen having a particularly specificity must not be confused with a virus antigen having a different specificity, and the same applies to the detection of erythrocyte or cell antigens or antibodies.

Another object of the invention is to provide a method of analysis which does not cause pollution.

Another object is to provide a method of analysis for substantially reducing the period required for obtaining results.

Another object is to provide a method for analysis wherein the reactions save a large proportion of reagents.

According to the invention, in order to determine whether a biological medium contains virus antigens or erythrocyte or cell antigens or antibodies, a method of analysis is used involving immunological reactions between cells or particles, a serum and molecules with antigenic or antibody activity which coat the wall of a vessel, wherein the reaction of analysis is conducted in a vessel, the wall of which has a point of convergence or apex situated on the axis of symmetry of the vessel and the reaction medium is subjected to a centrifugal force substantially parallel to the aforementioned axis under conditions such that in a first period all the cells or particles, whether they characterize a reaction with positive or negative result, progressively stick to and remain stuck to the wall of the vessel and then, in a second period, only the cells or particles characterizing one kind of reaction are stick-bounded to the wall of the vessel whereas the cells or particles characterizing the other kind of reaction are collected at the apex of the vessel.

More specifically, a reaction medium containing the cells or particles and an antiglobulin is introduced into the vessel, on the wall of which molecules capable of an immunological reaction with the antiglobulin have been fixed, and the reaction medium is subjected to a centrifugal force substantially parallel to the aforementioned axis under conditions such that at least the cells showing a positive reaction with a positive result, progressively stick to and remain stuck to the vessel wall by bonding forces of a first kind, i.e. immunological bonding forces involving the antiglobulin, which are added to bonding forces of a second kind, whereas the cells showing a negative reaction at the end of centrifuging are not stuck to the wall except by bonding forces of the second kind, so that the last-mentioned cells are collected at the apex of the vessel by applying a centrifugal force sufficiently strong the destroy the bonding forces of the second kind (i.e. connecting a negative cell to the vessel wall) but not sufficient to destroy the sum of the bonding forces of the first kind and the bonding forces of the second kind (i.e. connecting a positive cell to the vessel wall).

The method according to the invention defined hereinbefore involves a special kind of reactions, i.e. "immuno-adhesion" or "immuno-sticking" reactions. These reactions are so called because the reaction-indicating phenomenon consists of adhesion between (a) cells, erythrocytes or particles and (b) the bottom of a vessel covered with a mat of molecules having an antigenic or antibody activity. The adhesion is immunological since it is brought about by the production of antigen/antibody bonds between the corpuscles, cells or particles and the vessel.

It has been found that the method according to the invention results in a very great increase in sensitivity (from a factor of 100 to a factor of 1000) compared with known methods. It also greatly reduces the time for obtaining analytical results, so that urgent diagnoses can be made e.g. in 6 minutes instead of an hour in order to detect erythrocyte antigens or antibodies in blood. The method according to the invention also saves a very considerable proportion of reagents, which is very important particularly when the reagents used are as expensive as lymphocyte cells or rare specific test sera.

Furthermore, since the method according to the invention does not use any radio-activity techniques, it is much less expensive than radio-immunological methods and, unlike them, causes no pollution.

BRIEF DESCRIPTION OF THE DRAWINGS

The invention will be more clearly understood from the following description given by way of example and with reference to the accompanying drawings in which:

FIGS. 1-9b diagrammatically show the various steps in the method according to the invention, used for detecting $HB_s$ antigen in a blood sample;

FIGS. 11-14b diagrammatically show the various steps in the method according to the invention, used for detecting "D" antigen in erythrocytes of a sample of human blood.

DETAILED DESCRIPTION OF THE INVENTION

Figure 4A:
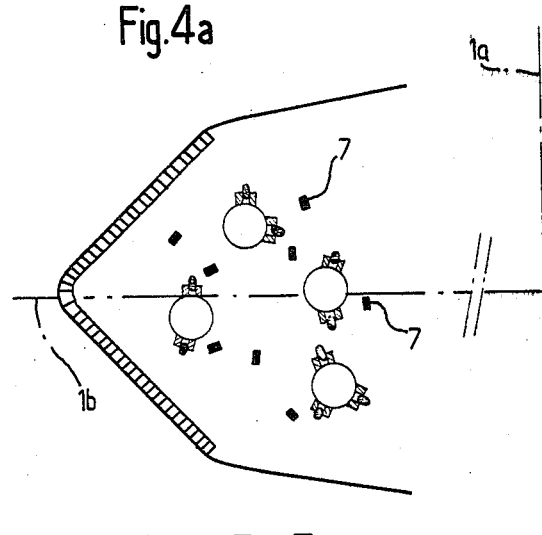

First Example for Carrying Out the Method According to the Invention

The first embodiment of the method according to the invention is described hereinafter with reference to FIGS. 1-9b. In this case the method is used to find whether the serum (or plasma) of a human blood sample contains $HB_s$ virus antigen, or "$HB_s$ antigen" for short.

(a) The first step of the method consists in preparing the bottom surface of a vessel for showing the adhesion or non-adhesion of cells or particles.

The vessel, the bottom of which must have a lower point of convergence on an axis of symmetry of the vessel, is in the present case a plastic cup 1, made e.g. of PVC (polyvinyl chloride) having a bottom 2 which has a V-shaped cross-section. Bottom 2 is covered with a mat of immunoglobulins 3 or IgX I, which in the present case are goat immunoglobulins in the immunochemical class G, or goat IgG (FIG. 1). The goat IgG immunoglobulins 3 are shown as white rectangles in the drawing.

THE IgG can be fixed on the plastic cup by various chemical methods, e.g. by producing carbo-diimide bonds between the plastic and the IgG molecules, or by simple adsorption of IgG by the plastic.

The concentration of IgG to be introduced is not critical, but since the sensitivity of the reactions depends on the density of immunoglobulins fixed on the surface, the solution used contains a sufficient quantity of immunoglobulins for the bottom of the cup to be saturated therewith, so as to obtain maximum sensitivity. After the goat IgG immunoglobulins have been fixed on the bottom of the cup, the cup coated with IgG is washed with physiological solution, e.g. with 9% NaCl solution, to remove any IgG not fixed on the cup. The cup is washed by sending physiological solution through it several times.

A small quantity of physiological solution is left at the bottom of the cup, to prevent the mass of IgG fixed on the plastics cup from drying. In this manner, the mat of IgG remains active for several hours.

(b) Next, the cells or particles (which we shall call reagent cells or particles) are prepared in order to demonstrate adhesion or non-adhesion depending whether the reaction is positive or negative, i.e. whether the serum under analysis contains or does not contain $HB_s$ antigen. In the example described here, the cells are sheep erythrocytes diamgrammatically shown at 4.

Immunoglobulins are fixed on erythrocytes 4 and must be from the same animal species and the same immunochemical class as the IgX I immunoglobulins fixed on the cup. Some of them must also have an antibody activity against $HB_s$ antigen. Advantageously the immunoglobulins are fixed at the same time as the erythrocytes are treated with chromic chloride, enabling them to fix protein molecules. In the present example, therefore, anti-$HB_s$ goat IgG immunoglobulins are fixed on the erythrocytes and are diagrammatically shown at 5 in the form of shaded rectangles. This step (fixing IgG on the erythrocytes) is diagrammatically shown in FIG. 2.

The anti-$HB_s$ goat IgG immunoglobulins are obtained from a goat serum injected with purified $HB_s$ antigen.

The thus-prepared erythrocytes constitute the "reagent erythrocytes". Of course, erythrocytes can be replaced by any other kind of cells or particles on which immunoglobulins can be fixed.

(c) After thus being prepared and suspended in physiological solution, the sheep erythrocytes 4 are incubated with the serum or plasma of the blood sample under analysis, to find whether it contains $HB_s$ antigen or not. In practice, the plasma used is e.g. diluted to 2% or 1%.

The incubation reaction, which is brought about outside the prepared cup, consists in contacting a suspension of sheep erythrocytes, prepared as described in the previous step, with the serum of the blood sample, incubation being performed at ambient temperature for a time varying from a few minutes to a few tens of minutes. The incubation step is diagrammatically indicated in FIG. 3, the $HB_s$ antigen being represented in the form of finely-shaded oval molecules 6.

In the case where $HB_s$ antigen is present in the serum to be analysed, the antigen molecules 6 become fixed on the anti-$HB_s$ IgG 5, which have already become fixed on erythrocytes 4. As diagrammatically indicated in FIG. 3, the antigen molecules settle around the anti-$HB_s$ IgG molecules fixed on an erythrocyte and thus produce steric congestion in the spaces between the anti-$HB_s$ IgG molecules.

In the case where the serum under analysis does not contain $HB_s$ antigen, no reaction occurs and the erythrocytes remain in the same state as at the end of the previous step, during which the fixed anti-$HB_s$ goat IgG, and no steric congestion occurs around the anti-$HB_s$ IgG molecules.

The thus-produced erythrocytes are advantageously washed several times with physiological solution (by introducing the solution, return to suspension, centrifuging, settling, throwing away the supernatant liquid, etc.) in the incubation vessel.

Figure 4B:
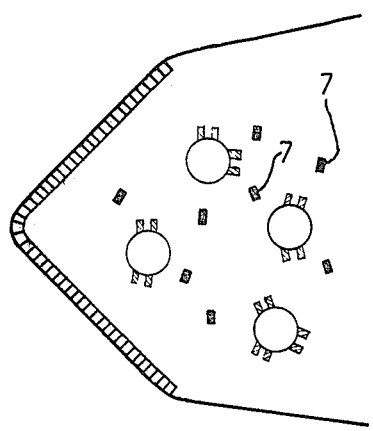

(d) Next, the incubated, washed sheep erythrocytes are introduced into cup 1, having a bottom 2 bearing the mat of goat IgG 3, simultaneously with an antiglobulin, i.e. an immune serum containing immunoglobulins having a specific antibody activity against the immunoglobulin fixed on the cup and on the erythrocytes, i.e. anti-IgX I Ig II immunoglobulins. In the example, an anti-goat rabbit antiglobulin is added containing antigoat IgG rabbit immunoglobulins G (or IgG), the immunoglobulins being diagrammatically indicated by small black rectangles 7 in FIGS. 4a and 4b. FIG. 4 shows a positive reaction whereas FIG. 4b shows a negative reaction.

Alternatively, the suspension of erythrocytes can be introduced into the cup, followed by the antiglobulin.

The antiglobulin immunoglobulins have an antibody function which is at least divalent towards goat IgG, i.e. an anti-goat IgG rabbit IgG can react via one antibody function with a goat IgG molecule fixed to the bottom of the cup, whereas another such function can react with an anti-$HB_s$ goat IgG molecule fixed on an erythrocyte. The immunoglobulins, which have a specific antibody activity towards goat IgG immunoglobulins, are supplied from the serum of an animal of a different species (a rabbit in the present case) which has been injected with goat IgG, preferably purified.

As explained hereinafter, the antiglobulin was used here at a relatively high concentration, e.g. a goat anti-IgG antiglobulin having a strength of at least 128 in the Coombs method and either pure or slightly diluted (dilution ratio $\frac{1}{2}$ or $\frac{1}{4}$).

During the entire incubation (the "antiglobulin" incubation) which, for reasons to be explained, must be very short, the cup is preferably continuously agitated to obtain a uniform mixture of antiglobulin and erythrocytes in suspension.

(e) Antiglobulin incubation is followed by centrifuging, which must be performed under exact conditions in order to demonstrate adhesion or non-adhesion depending whether the sample of serum incubated with pretreated sheep erythrocytes contains or does not contain $HB_s$.

The centrifuging, which is performed by rotating the cup around an axis $1a$ perpendicular to the cup axis of revolution $1b$, comprises a first step or "laying-on" step, which is started sufficiently quickly after the beginning of antiglobulin incubation, i.e. after introducing the suspension of erythrocytes and antiglobulin into the cup, to ensure that only a little IgG 3 fixed on the cup or IgG 5 fixed on the erythrocytes has reacted with an anti-goat IgG IgG 7 of the antiglobulin. It has been found that the first centrifuging step should preferably start after a time not greater than the time for 10% of the goat IgG to react with the goat anti-IgG immunoglobulin on the antiglobulin. In practice, centrifuging is started between a few seconds and a few tens of seconds after the antiglobulin incubation begins.

During the first centrifuging step, the reaction medium containing the suspended sheep erythrocytes and antiglobulin is laid under pressure against the bottom surface 2 of the cup so that the anti-$HB_s$ goat IgG 5 carried by the processed, incubated sheep erythrocytes are placed opposite the goat IgG 3 fixed on the plastic, causing the erythrocytes to rapidly and initially adhere or stick to the bottom of the cup by the immunoglobulins 7 of the antiglobulin, which become fixed to the IgG 5 and to the IgG 3. The rapid initial adhesion occurs whether the reaction is positive or negative, i.e. whether $HB_s$ antigen molecules are or are not fixed to the erythrocytes by anti-$HB_s$ goat IgG 5. This is brought about by using a first moderate centrifuging speed, the speed being determined as explained hereinafter.

Figure 5A:
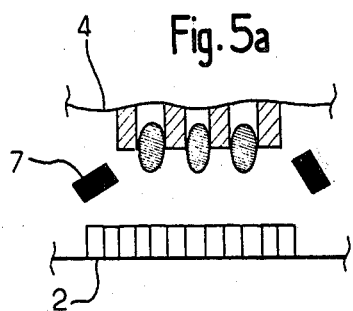
Figure 5B:
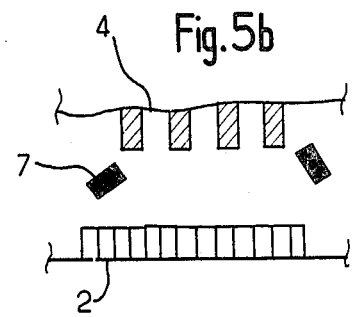

FIGS. 5a, 5b are very large-scale diagrams of the facing surfaces of an erythrocyte 4 and the bottom 2 of the cup during the laying-on step. FIG. 5a corresponds to a positive reaction whereas 5b corresponds to a negative reaction.

In both cases, antiglobulin immunoglobulins Ig 7, owing to their antibody specificity towards goat IgG, come between IgG 5 fixed on the erythrocytes and goat IgG 3 fixed on the bottom of the cup. During this laying-on operation, which results in moderate adhesion of the erythrocytes to the bottom surface 2, corridors or recesses form between the plastic and the erythrocytes, the corridors being limited by chains of IgG 5/Ig 7/IgG 3 molecules which have formed. The corridors act as filters restricting the approach of other Ig 7 molecules.

As mentioned, the corridors form both in the case of a positive reaction, i.e. when the sheep erythrocytes 4 have been able to fix $HB_s$ antigen molecules 6 via IgG 5, and in the case of a negative reaction in which the erythrocytes 4 have not been able to fix virus antigen molecules. However, in the case of a positive reaction (see FIG. 6a), the corridors are obstructed by virus antigen molecules whereas they are not obstructed in a negative reaction (see FIG. 6b).

In practice, the first centrifuging step is at an acceleration of approx. 200 g (g being the gravitational acceleration) for about 40 to 60 seconds, the reaction being brought about in a cup having a cone aperture angle of 120°.

(f) Next, centrifuging is stopped for a few minutes. During this stoppage, the free Ig 7 molecules flow in the corridors previously formed during the laying-on operation and can thus become fixed on any remaining free erythrocyte IgG 5 or substrate IgG 3. This phase (i.e. stoppage of centifuging) is in fact a prolongation of antiglobulin incubation.

We have seen that, during the moderate laying-on brought about during the first centrifuging step, connecting chains made up of an IgG fixed on the vessel, an anti-IgG molecule and an IgG fixed on to an erythyrocyte form between the vessel and the erythrocyte. The inventor, during experiments connected with the invention, has found that this configuration is less stable with regard to energy, in the presence of an excess of anti-IgG molecules, than the configuration comprising an IgG fixed on to the vessel, an anti-Ig molecule, . . . , an anti-IgG molecule and an IgG fixed on to an erythrocyte. It is therefore reasonable to assume that if the duration of antiglobulin incubation is prolonged, the final result is to form a larger number of IgG/anti-IgG . . . anti-IgG/IgG configurations than IgG/anti-IgG/IgG configurations which will result in "unsticking" of erythrocytes from the vessel. We have made use of this finding.

When the reaction medium is at rest, antiglobulin incubation continues and the anti-goat IgG 7 react with the goat IgG 3 or 5 to form the most stable configuration.

Figure 6A:
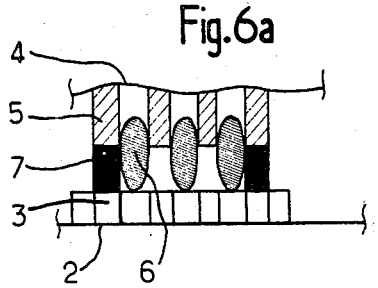
Figure 6B:
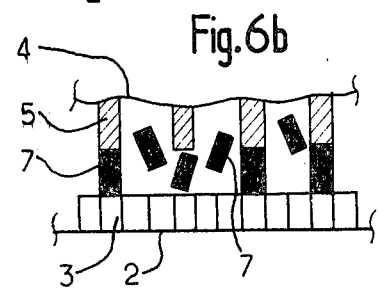
Figure 7A:
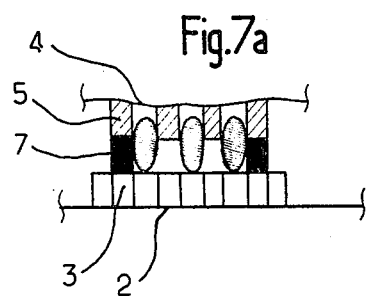
Figure 7B:
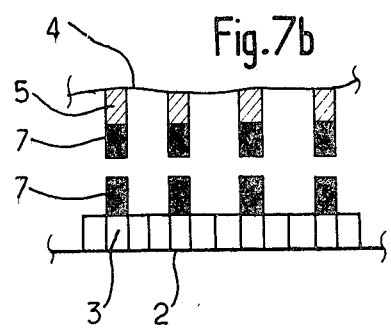
Figure 8A:
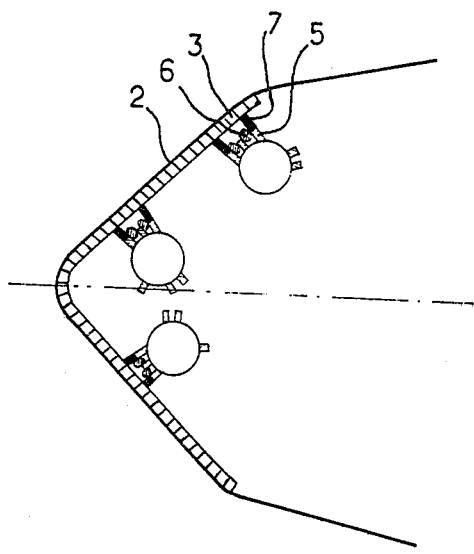
Figure 8B:
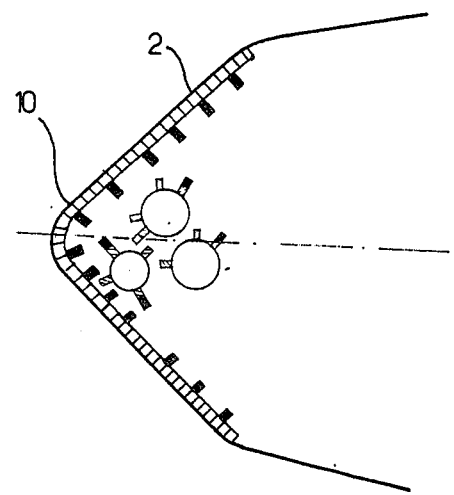
Figure 9A:
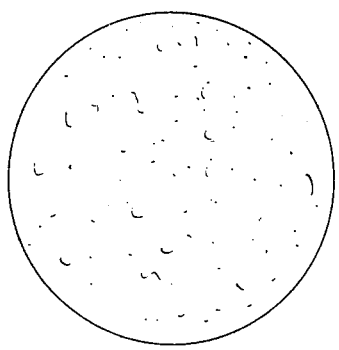
Figure 9B:
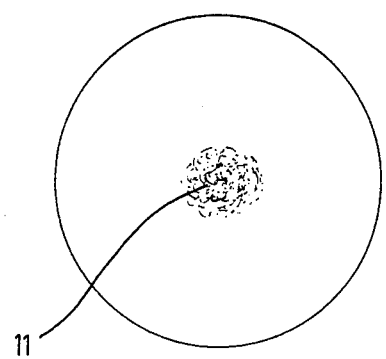

However, since (as explained hereinbefore) the corridors produced between erythrocytes and the plastic are much more obstructed in a positive reaction than in a negative reaction, there is a much larger flow of free molecules Ig 7 in the corridors formed in a negative reaction (see FIG. 6b) than in a positive reaction (see FIG. 6a). Consequently the facing surfaces of the erythrocytes and the plastics in the corridors are much more quickly saturated with Ig 7 (fixed on the erythrocyte IgG 5 or the plastic IgG 3) in a negative reaction than in a positive reaction. After a while, in a negative reaction (FIG. 7b), the facing surfaces of the erythrocytes and the plastic have a majority of configurations such as the following:

Plastic+goat IgG 3/anti-goat IgG rabbit Ig 7 . . . anti-goat IgG rabbit Ig 7/goat IgG 5+erythrocyte. Since two molecules of similar nature face one another, this configuration cannot result in the formation of a complete molecular bridge consisting of plastic+goat IgG 3/anti-goat IgG rabbit Ig 7/goat IgG 5+erythrocyte.

Since the configurations formed during the prolongation of antiglobulin incubation are mostly of this kind, the molecular bridges which formed between the plastic and the erythrocytes during the rapid initial adhesion resulting from the laying-on step are no longer present in sufficient number to maintain the adhesion and there results "unsticking".

On the other hand, the saturation of the facing erythrocyte and plastics surfaces by the Ig 7 is much slower for a positive reaction (FIG. 7a) and consequently the fixation of anti-IgG molecules on to IgG has not reached the level sufficient to unstick the erythrocytes by the time when unsticking occurs in a negative reaction.

Consequently, the length of the centrifuging-stop phase or prolongation of antiglobulin incubation is adjusted so that the amount of saturation of the facing erythrocyte and plastics surfaces by the Ig 7 molecules is sufficient to cause unsticking in the case of a negative reaction but not in the case of a positive reaction.

(g) This is followed by the last centrifuging step, which is carried out at a speed $V_2$ greater than speed $V_1$. This centrifuging step is used to show the difference between a positive and a negative reaction. Speed $V_2$ is chosen so that the resulting centrifugal force drives the erythrocytes most saturated with Ig 7, i.e. the erythrocytes giving a negative reaction, to the cup apex 10 and collects them there (FIG. 8b) but does not drive the erythrocytes of a positive reaction, which remain fixed to the cup wall owing to the persistence of the molecular bridges, i.e. plastics+goat IgG 3/anti-goat Ig rabbit Ig/goat IgG 5+erythrocyte (FIG. 8a), the aforementioned molecular bridges being efficiently protected since the prolongation of antiglobulin incubation stops before the amount of saturation in Ig 7 of antiglobulin is sufficient to cause unsticking.

In practice, when the cup used has a cone aperture angle of 120°, a second configuration is brought about at an acceleration of approx. 500 g for about 40 seconds.

The analytical results can thus be observed immediately after stopping the second centrifuging step.

Thus, in the case of a positive reaction, i.e. when the sample of serum used for incubating the sheep erythrocytes does in fact contain $HB_s$ antigen, the erythrocytes remain fixed to the bottom of the cup via IgG 3, Ig 7 and IgG 5. In that case, if the cup is considered along its 1b axis (FIG. 9a) the homogeneous mono-layer of erythrocytes is distributed over the entire bottom of the cup and adhesion occurs.

If, on the other hand, the analyzed sample of serum does not contain $HB_s$ antigen, the erythrocytes, as described previously, are driven to the apex of the cup and collect there. Consequently, if the cup is examined along its axis, a micro-deposit of erythrocytes is observed (FIG. 9b) and no adhesion occurs.

The amounts of reagents used are not critical. For example, in a cup having a diameter between 1 and 7 mm, the volume of liquid introduced is between 15 and 250 μl; the suspension of erythrocytes and the antiglobulin are advantageously introduced in equal volume.

As shown by the description of the method according to the invention, some steps must be performed under precise conditions.

The antiglobulin concentration used depends on the surface density of IgG in the reagent erythrocytes obtained during step (b), as explained hereinafter with reference to the second sample application of the method according to the invention.

The concentration must be sufficiently high to ensure (a) rapid initial adhesion of the erythrocytes to the vessel during the first centrifuging step and (b) provide an excess of anti-IgG molecules which, if required, can cause the erythrocytes to unstick in a negative reaction, as explained in connection with step (f) hereinbefore. Furthermore, the concentration of antiglobulin must be moderately high to prevent an excessive number of molecular bridges forming between erythrocytes and the vessel during the laying-on step, since even in a negative reaction, such bridges will form small corridors interfering with the flow of anti-IgG molecules during the stoppage of centrifuging.

During the immuno-adhesion reactions, a "zone phenomenon" dependent on the antiglobulin concentration, i.e. a considerable variation in the sensitivity of the immunoadhesion reaction around a maximum corresponding to a certain concentration of antiglobulin, has been observed side by side with a zone phenomenon dependent on the time of contact between the antiglobulin and the IgG before centrifuging. The zone phenomenon depending on the contact time, which has a more important effect on the sensitivity of the reaction than the zone phenomenon dependent on the concentration of antiglobulin, can be explained as follows:

During antiglobulin incubation, the anti-IgG molecules supplied by the antiglobulin become fixed to (a) the IgG fixed to the erythrocytes and (b) the IgG fixed to the plastic cup, the number of fixed anti-IgG molecules being dependent on the incubation time. As mentioned, the antiglobulin incubation phase is followed by a first centrifuging step or "laying-on" step. As the duration of incubation increases, it is correspondingly more likely that an anti-IgG molecule previously fixed on an erythrocyte will be brought during the laying step opposite a similar molecule, i.e. an anti-IgG molecule which is fixed to the plastic. This configuration (erythrocyte+IgG/anti-IgG . . . anti-IgG/IgG+plastic), which is brought about during the laying-on of the erythrocyte on the bottom of the cup, clearly has an adverse effect on the adhesion of the erythrocyte to the plastic. It can be seen that the frequency of formation of the anti-sticking configurations increases with the duration of antiglobulin incubation and consequently that the chances of adhesion, i.e. the sensitivity of the reaction, decrease in proportion to the duration of antiglobulin incubation.

However, the sensitivity is not at a maximum when the incubation time is zero since, for the adhesion to be physically obtainable and perceptible, some anti-IgG molecules must already be fixed to one of the end links (i.e. to the IgG fixed to the erythrocytes or to the IgG fixed to the plastics) at the moment of the laying-on. In practice, a few seconds or fractions of a second are sufficient for these few anti-IgG molecules to become fixed.

Advantageously this very short incubation time is determined experimentally so that, during the step immediately following anti-globulin incubation, i.e. the laying-on step, all the reactions, whether positive or negative, result in adhesion. Accordingly, the various aforementioned process steps are carried out on a negative reaction, i.e. in the present example by using a sample of serum not containing $HB_s$ antigen, the appropriate duration of incubation being that which is sufficient to obtain 100% adhesion during the laying-on step.

During antiglobulin incubation, immuno-adhesion is extremely sensitive to slight decreases in the surface density of IgG fixed to the plastic and still free from anti-IgG molecules.

Figure 10:
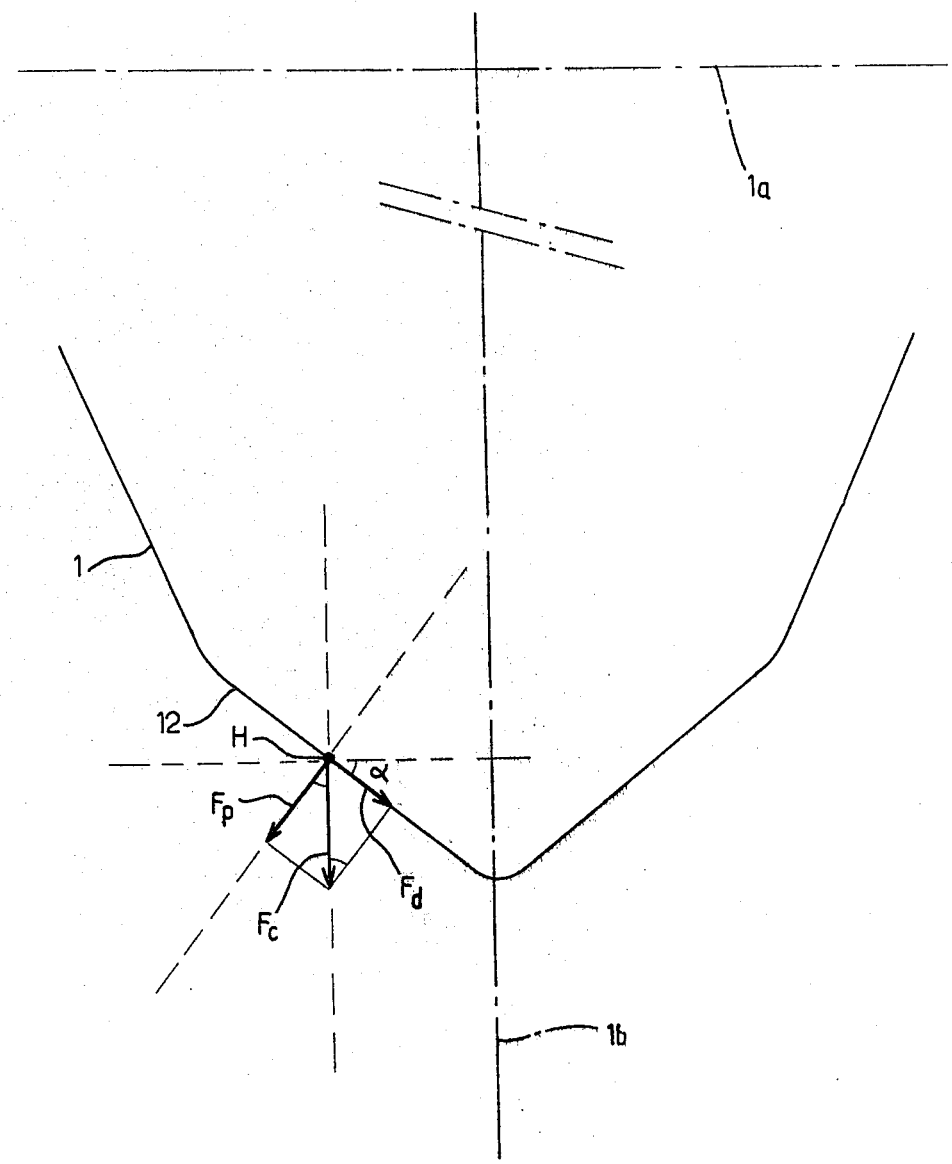
FIG. 10 is a diagram of the forces to which a cell is subjected during centrifuging.

As we have seen, the centrifuging step is complex and occurs in a number of phases, each of which has a particular mechanical effect on the reactions. Before giving a more detailed explanation of the exact conditions required during these centrifuging phases, we shall consider the forces occurring during centrifuging, with reference to FIG. 10.

If an erythrocyte H or any other cell or particle which may be appropriately used for demonstrating adhesion or nonadhesion, is centrifuged by rotation around an axis $1a$ perpendicular to the axis of revolution $1b$ of the cup, the particle is subjected to a centrifugal force $F_c$ parallel to the cup axis $1b$. A number of other parameters are involved, as defined hereinafter:

(1) The angle $\alpha$ between a generatrix of the cup cone and its projection on to a plane perpendicular to the direction of the centrifugal force. This is called the "slope" angle;

(2) The mass m of an erythrocyte;

(3) The number n of g applied for a centrifuging operation at a speed of V rpm;

(4) The time t during which the speed is applied;

(5) The sum of the "non-specific forces" (French abbreviation FNS) holding an erythrocyte against the plastic. The sum is made up of the electrostatic forces attracting an erythrocyte to the plastic, immunochemical bonds having a specificity which "interferes" with the main specificity involved in the reaction, and forces which prevent detachment since the cell or particle bears on local obstacles such as irregularities in the cup or adjacent cells or particle in the sloping position);

(6) The sum of the specific bonding forces (French abbreviation FS) holding an erythrocyte on the slope of the cup. These forces result from the chain of bonds fixing the plastics to the erythrocyte, i.e.:

IgG (fixed to the plastics)/anti-IgG molecule/IgG (fixed to the erythrocyte);

(7) The pressing force exerted on an erythrocyte at a speed of V rpm, i.e. the force pressing the erythrocyte against the plastic, depending on the centrifugal force component perpendicular to a cone generatrix. The pressing force (symbol $F_p$) is equal to $n \times m \times \cos \alpha$;

(8) The detachment force exerted on the erythrocyte at a speed of V rpm, i.e. the force exerted by the centrifugal force component parallel to a cone generatrix and tending to tear the corpuscle loose. The detachment force (symbol $F_d$) is equal to $n \times m \times \sin \alpha$.

Using these general considerations, we shall now explain the phenomena occurring during the various centrifuging steps.

In the previous example, during the first centrifuging step or laying step, an attempt is made to obtain rapid initial adhesion of erythrocytes, resulting in the formation of corridors between the facing surfaces of the plastics and erythrocytes. As already explained, these corridors act as filters restricting the approach of additional anti-IgG molecules.

Consequently, the speed $V_1$ of the first centrifuging step is chosen so that the pressing force $F_{p1}$ is sufficient to stick all the erythrocytes in all the reactions, whether positive or negative. Speed $V_1$ must therefore be chosen so that the detachment force $F_{d1}$ is insufficient to break the bonding forces holding the erythrocytes to the bottom of the cup.

When the erythrocytes stick to the plastics, the corridors must be able to act as filters during the subsequent step, when centrifuging is stopped or continued at a very slow rate. Consequently, the speed $V_1$ must be sufficiently low to prevent the laying-on operation from excessively squeezing the erythrocytes against the bottom of the cup, since if the laying-on operation is too energetic and the erythrocytes are squeezed against the plastic, the corridors will also be squeezed out of existence, even in negative reactions. The free anti-IgG molecules will no longer be able to flow between the plastic and the erythrocytes, and this will prevent saturation of the facing surfaces of the erythrocytes and plastic by anti-IgG molecules. The saturation phenomenon has already been described in connection with the various steps of the method.

On the other hand, the speed $V_1$ during the laying-on step must not be too low, since the result will be that the reagent components, i.e. the IgG fixed to the corpuscles and the IgG fixed to the plastics, will not approach sufficiently near and adhesion will be insufficient and the corridors will not form properly.

The second centrifuging step occurs at a speed $V_2$ greater than speed $V_1$. The second step does not start immediately after the laying-on step but after a certain idle time which, as already explained, prolongs the antiglobulin incubation. The centrifuging speed $V_2$ must be sufficient for the erythrocytes which have fixed the largest number of anti-IgG molecules during the antiglobulin incubation prolongation step, i.e. the erythrocytes characterising a negative reaction, to be driven to the apex 10 of the bottom of the cup, but must not drive the erythrocytes characterising a positive reaction since, as already explained, these remain stuck to the bottom walls of the cup after the antiglobulin incubation prolongation step, i.e. after the stoppage of centrifuging. Consequently, speed $V_2$ is made such that the resulting detachment force $F_{d2}$ applied to an erythrocyte is greater than the sum of the non-specific bonding forces, which are thus the only forces retaining a negative-reaction erythrocyte to the bottom of the cup. However, force $F_{d2}$ must be less than the sum FNS+FS of the non-specific bonding forces and the specific bonding forces, which hold the positive-reaction erythrocytes against the cup.

In that case, only the negative-reaction erythrocytes will come loose and collect at the cup apex, whereas the positive-reaction erythrocytes will remain stuck. This results in a very clear distinction between positive and negative reactions.

Accordingly, the optimum values of the previously-defined parameters involved in centrifuging, at which the reaction will give the best results, can be determined for each system under study, i.e. for a particular kind of reagent cells or reagent particles used, depending on the virus antigen to be detected and the IgX I and anti-IgX I molecules involved in the reaction. Accordingly, the ratio of the detachment force $F_d$ to the pressing force $F_p$ and expressing the possibility of detachment, is equal to: $(n \times m \times \sin \alpha)/(n \times m \times \cos \alpha)$, i.e. $\tan \alpha$. This value therefore depends only on the slope $\alpha$.

Consequently if $\alpha = 0°$, $\tan \alpha$ is zero and the possibility of detachment is zero. On the other hand if $\alpha = 90°$, $\tan \alpha$ is infinite and so is the possibility of detachment, i.e. non-detachment is impossible.

Consequently, intermediate values of the angle $\alpha$ can be used for varying the ratio of the detachment force to the pressing force and adapting it to the nature of the reagent cells or particles, the virus antigen and the IgG I and anti-IgG I molecules involved, so as to obtain specific detachment of the negative-reaction reagent cells or particles during the second centrifuging step.

In order, therefore, to work under optimum conditions, it is advantageous to use sets of cups having different slopes, in order to choose the cup having the most suitable slope α for the reaction in question.

Consequently, reactions for analyzing a number of different samples in which virus antigens having various nature and specificity have to be detected, can be carried out simultaneously under the same centrifuging conditions, i.e. applying the same centrifugal force, if the cup chosen for each different sample for analysis has a bottom having a slope α such that the negative-reaction reagent cells or particles will be detached by applying the available centrifugal force chosen for the second centrifuging step.

Accordingly, the invention provides sets of cups having a V bottom and different cone aperture angles, varying e.g. from 80° to 140° in steps of 10°.

Thus, in the previously-described example for detecting $HB_s$ virus antigen in a blood sample, it is advantageous to use cups having a conical bottom and a cone aperture angle of 120°.

Figure 15:
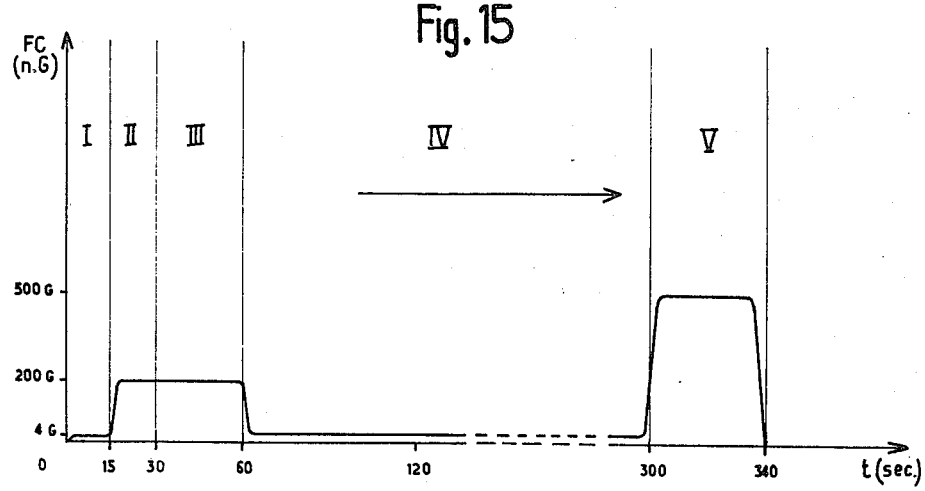
FIGS. 15-18 are centrifuge diagrams.

FIG. 15 is a diagram illustrating the various centrifuging steps during a reaction for detecting $HB_s$ antigen in a human blood sample, the immuno-adhesion reaction being carried out in a cup having a conical bottom and a cone aperture angle of 120°. The ordinate shows the applied centrifugal force in g and the abscissa shows the time in seconds.

The reaction medium, comprising the erythrocytes incubated with the serum sample and the antiglobulin, is introduced into the cup, the bottom of which is coated with goat IgG, and antiglobulin incubation is allowed to proceed. As previously stated, the cup is continuously agitated during incubation, e.g. by reciprocation in a direction parallel to the axis of rotation. This is the agitatin and antiglobulin incubation step indicated by I in FIG. 15. In the present case, the step is performed during 4 g centrifuging—a value which has no effect on the fall of the erythrocytes or the manner in which they lay on the bottom of the cup. The value of 4 g is maintained for 15 seconds.

Next, the centrifuging acceleration is quickly increased to 200 g and maintained at the same value up to the 60th second after the reaction medium has been introduced into the cup. Accordingly, the 15th second begins phase II of the fall of the erythrocytes, all of which have touched the bottom of the cup by the 30th second. Centrifuging is continued at 200 g and the falling step is followed by a step III during which the erythrocytes lay on the bottom of the cup. All the erythrocytes, both those in positive reactions and in negative reactions, stick to the bottom of the cup and "filtering corridors" form between the bottom surface and the coating of erythrocytes.

The 60th second is the beginning of the diffusion phase between the plastics and those erythrocytes of anti-goat IgG molecules which are still flowing freely in the reaction medium. As previously explained, this step (step IV in FIG. 15) is a prolongation of antiglobulin incubation. This step is brought about during centrifuging at 8 g acceleration, a value which does not have sufficient centrifugal effect to squeeze the corridors formed during the preceding step III. During step IV the facing surfaces of the erythrocytes and the bottom of the cup become progressively saturated by anti-goat IgG molecules. The threshold at which the negative-reaction erythrocytes come unstuck as a result of saturation is reached at the 300th second.

The last step (i.e. during which the negative-reaction erythrocytes, if any, collect at the apex of the cup) is brought about by rapidly increasing the centrifuging acceleration to 500 g, which is sufficient to drive the negative-reaction erythrocytes which, as a result of the saturation with antiglobulin, have practically come unstuck at the end of step IV. During the last step (step V) the erythrocytes which have come unstuck during the preceding step are rapidly collected.

The last centrifuging step is stopped when, in the case of a negative reaction, the percentage of detached erythrocytes is just sufficient to indicate a true negative reaction. In the present example, the last centrifuging step is stopped at the 340th second.

The values of the parameters for each step (i.e. the centrifuging speed and duration) can be determined in advance during tests on a typical negative reaction, using the same reagents. The test giving the best results will provide the parameter values which will be applied during the real analysis reaction.

Alternatively, centrifuging is servo-controlled during the reactions, and the process is applied simultaneously to a cup in which the sample-analysis reaction is being carried out and a cup in which a negative control reaction occurs and is illuminated by a stroboscopic flash during each centrifuging revolution.

A magnified image of the bottom of the control-reaction cup is filmed by a television camera and analysed e.g. once per second. The surface and opacity of the micro-deposit image forming as a result are measured and the growth curve of the micro-deposit is compared with the curve for the micro-deposit obtained in a reference negative reaction. Thereupon, the centrifuging speed and time is controlled so that the growth curve of the micro-deposit in the negative control reaction corresponds to the reference growth curve.

Centrifuging is finally stopped when the surface of the analysed micro-deposit corresponds to a quantity of detached erythrocytes at least equal to the quantity representing the discrimination threshold of a true negative reaction. This quantity is defined as follows:

During previous tests on negative control reactions, a measurement is made of the percentage of erythrocytes contained in a micro-deposit having the minimum size to be significant of a true negative reaction, i.e. which can be distinguished, measured and reproduced. Next, the standard deviation σ for these negative reactions is determined. The resulting discrimination threshold for a negative reaction occurs when the percentage of erythrocytes collected in a micro-deposit is equal to the aforementioned significant percentage for a negative reaction, plus twice the standard deviation. Similarly, the discrimination threshold of a positive reaction occurs when the percentage of erythrocytes collected in a micro-deposit is equal to the significant percentage for a negative reaction, minus twice the standard deviation.

If, for example, the average percentage of erythrocytes in a micro-deposit for a negative reaction is 12% and the standard deviation is evaluated at 3%, the discrimination threshold of a negative reaction is $12\% + 2 \times 3\% = 18\%$. Accordingly, if the surface of the micro-deposit resulting from the analysis reaction corresponds to 18% or more erythrocytes which have been detached and have collected at the cup apex, the reaction is considered to be definitely negative. The discrimination threshold for a positive reaction is equal to 12% minus $2 \times 3\% = 6\%$. Consequently, if the surface of the micro-deposit resulting from the analysis corresponds to 6% or fewer erythrocytes in the micro-deposit, the reaction is considered definitely positive. If the surface of the micro-deposit corresponds to between 6 to 18% erythrocytes, the reaction is considered doubtful and has to be repeated.

We have described a first example for carrying out the method according to the invention for detecting the presence of $HB_s$ virus antigen in a human blood sample. Of course, the same method can be used for detecting any other virus antigen in a blood sample if a suitable choice is made of the nature of the reagent cells or particles, the nature of the IgX to be fixed to the bottom of the cup and to the aforementioned cells or particles, and the nature of the anti-IgX I molecules.

The method according to the invention is also applied to biological media other than blood—e.g. saliva or urine—in order to detect virus antigens or, more generally, antigens which may be called "molecular", i.e. free molecules not fixed to a cell and having antigenic properties, provided of course that the various reactions involved are suitably modified, i.e. with regard to the reagent cells or particles, the immunoglobulins to be fixed to the cells or particles and to the cup, the antiglobulin, and the various other reaction parameters.

Second Example for Carrying Out the Method According to the Invention

We shall now, with reference to FIGS. 11–14b, describe a second application of the method, for determining whether erythrocytes from a human blood sample have "D" antigenic activity. Erythrocytes having this activity occur in "rhesus positive" patients, whereas erythrocytes not having this activity correspond to "rhesus negative" patients.

The following is a first embodiment of the second example:

(a) As in the first example, the first step consists in preparing the surface of the substrate for demonstrating adhesion or non-adhesion of the cells (FIGS. 11, 12).

The substrate is a plastics cup 21, e.g. of PVC (polyvinyl chloride) having a V-shaped bottom 22.

Bottom 22 is coated with a layer of immunoglobulins 23 which must without fail be from the same animal species and the same immunochemical class as the specific antibody immunoglobulins of the antigen which is to be detected in the erythrocytes. In the example, we wish to determine if the "D" antigen is present at the surface of the membrane of human erythrocytes. The specific antibody of this antigen is a human immunoglobulin, inter alia type G, containing the "anti-D" antibody unit. Accordingly, type G human immunoglobulins (i.e. human IgG) are fixed to the bottom of the cup. The human IgG are denoted by white rectangles 23.

The IgG are fixed on to the plastic cup under the same conditions as in the first example. After the IgG have been fixed to the bottom of the cup, they are washed with 9% NaCl solution, to remove all the unattached IgG.

The concentration of IgG to be introduced is not critical; preferably the amount is in excess of the quantity which can become fixed, e.g. using a 1 mg/ml solution.

A small amount of physiological solution is kept at the bottom of the substrate, to prevent the layer of IgG from drying on the plastic.

(b) In the present example, the cells being analysed are erythrocytes from a human blood sample immersed in physiological solution. They are placed in contact outside the cup, at ambient temperature and for a time between a few minutes and a few tens of minutes, with a test serum specific to the antigen activity to be detected, i.e. a serum containing IgG molecules having a known (anti-D) antibody specificity and capable of specifically becoming fixed to any "D" antigen radicals carried by the erythrocyte. The serum is called "anti-D test serum". In practice, use is made e.g. of a suspension of erythrocytes coming from a 2% or 1% dilute blood samle. The right part of FIG. 13a diagrammatically shows the incubation step in the case where the analyzed erythrocytes are "positive", i.e. bear "D" antigen radicals, which are symbolized by points on the membrane of erythrocytes 24. The antigen radicals of the erythrocytes fix "anti-D" antibody IgG molecules 25 from the test serum. The antibody IgG 25 imminoglobulins are represented by shaded rectangles and from a complex 26.

Figure 13B:
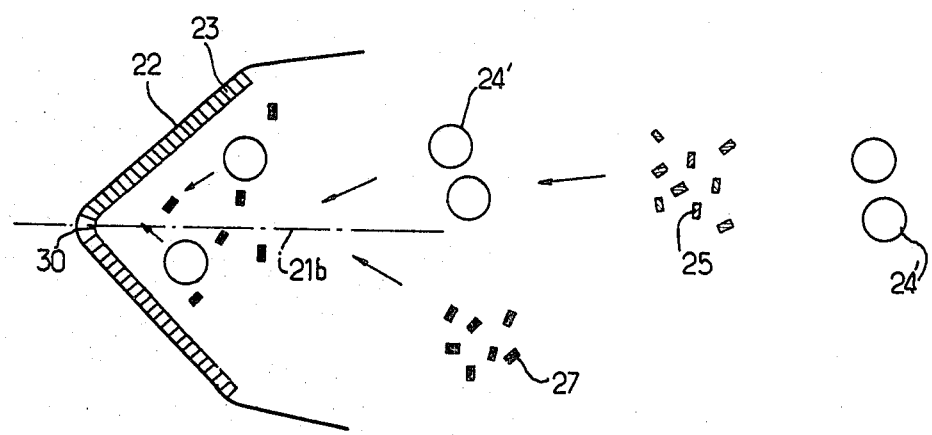

FIG. 13b is a similar diagram of the same step in the case where the erythrocytes 24' are "negative", i.e. do not carry erythrocyte radicals "D". In that case, the erythrocytes 24' do not fix the "anti-D" IgG 25.

Incubation is advantageously followed by a set of washing operations each comprising a number of rinsing operations (e.g. three) with physiological solution in the incubation vessel. Each rinsing operation comprises the following set of operations: introduction of physiological solution, formation of suspension, centrifuging, settling, and discarding of supernatant fluid. The product is a suspension of incubated erythrocytes which have been washed, i.e. immersed in a medium not containing free IgG 25.

(c) Next, the suspension of incubated, washed erythrocytes is introduced into the cup 21 (the bottom of which is lined with human IgG 23) simultaneously with an antiglobulin, i.e. a solution of animal immunoglobulins 27 presenting an antibody function against human IgG. The antiglobulin immunoglobulins 27 are diagrammatically represented by black rectangles.

Alternatively, the suspension of erythrocytes is first introduced into the cup, followed by the antiglobulin.

The antiglobulin used in the present case is an immune serum of a goat injected with human IgG. The immune serum provides immunoglobulins (called anti-human IgG goat Ig) presenting an antibody function which is at least divalent towards human IgG. Consequently, a anti-human IgG goat Ig can have one antibody radical fixed to a human IgG fixed to the bottom of the cup, and another radical fixed to a human IgG fixed to an erythrocyte.

The antiglobulin used here has a high concentration, since the sensitivity of the immuno-adhesion reaction is linked to the concentration of antiglobulin. One possible explanation of this phenomenon may be as follows. However long the antiglobulin incubation lasts in practice, there is much less than 100% saturation of IgG, either fixed to erythrocytes or to the cup. Consequently, the formation of a coat of erythrocytes results in bringing close together a large number of heterologous IgG molecules, i.e. IgG fixed to the cup and IgG fixed to the erythrocytes. However, as long as an erythrocyte is not held by adhesion, i.e. until the antiglobulin molecules have formed a bridge between the IgG fixed to the erythrocyte and the IgG fixed to the plastics, the erythrocyte moves or slides on the sloping bottom of the cup lined with IgG, so that the closest approach of any two heterologous IgG molecules lasts for a very short time, the time varying inversely with the surface density of IgG on the erythrocytes. Consequently, the time during which the distance favours a double reaction with an antiglobulin molecule is very short. The reaction will not occur if the average distance of an antiglobulin molecule nearest the two heterologous IgG molecules is too great for the average access time of the antiglobulin molecule to be shorter than the effective time during which two heterologous IgG molecules approach to within a favourable distance. Clearly, the mean access time can be reduced by increasing the concentration of antiglobulin.

Since the surface density of IgG in the erythrocytes cannot be known in advance, the antiglobulin must be used in high concentration to ensure that even if the erythrocytes have a very low surface density of IgG, the anti-IgG molecules can react with the few IgG present on the erythrocytes and stick them to the recipient. Incidentally, the effect of the antiglobulin concentration on the sensitivity of the reaction is less in the case when a virus antigen such as $HB_s$ antigen in being detected, since in this case the surface density of IgG in the reagent erythrocytes has been fixed at a relatively high level.

For example, use is made of a human anti-IgG antiglobulin having a strength of at least 128 in the Coombs technique, either pure or slightly diluted. In practice, the antiglobulin is diluted to the concentration which has been found to be optimum with regard to sensitivity in the other known processes of analysis, inter alia in the Coombs reaction involving haemaglulination.

Accordingly, the suspension of erythrocytes obtained after step (b) is incubated with the antiglobulin in the cup. If necessary, the cup is agitated during the process.

(d) Incubation is followed by centrifuging, which must be carried out under precisely-regulated conditions, since it is designed to cause or prevent adhesion, depending whether the erythrocytes are positive or negative.

As explained hereinbefore with reference to the first example of the method, antiglobulin incubation must be very brief. Accordingly, centrifuging is started between a few seconds and a few tens of seconds after the reaction medium (i.e. a suspension of erythrocytes and antiglobulin) has been introduced into the cup, i.e. after a sufficiently short time to ensure that only a very few IgG fixed to the bottom of the cup (IgG 23) or to the erythrocyte (IgG 25) if any, are occupied by antihuman IgG Ig molecules of the antiglobulin.

Centrifuging is performed by rotation around an axis 21a perpendicular to the axis of revolution 21b of cup 21, and in the following two stages:

During the first stage, the reaction medium is distributed and laid under pressure on the bottom surface 22 of the cup, so that all the erythrocyte/IgG complexes, if formed, or all the erythrocytes not modified by incubation with anti-D test serum are brought towards IgG fixed on to the plastics. This is done by applying a first centrifuging speed $V_1$ which is insufficient to drive the erythrocytes towards the cup apex 30.

In accordance with the general considerations given hereinbefore, the speed $V_1$ of the first centrifuging stage is chosen so that the detachment force $F_{d1}$ produced thereby is insufficient to break the non-specific bonding forces (French abbreviation FNS) holding the erythrocytes to the bottom of the cup. The erythrocytes being so pressed, they are in a position such that the anti-human IgG molecules of antiglobulin, if possible, can form a bridge between human IgG fixed to the plastics bottom and human IgG carried by the erythrocytes.

This "laying-on" stage is also used for moving any anti-human IgG molecules already secured to positive/IgG erythrocyte complexes towards any IgG sites which is still available on the plastics, i.e. into a position facilitating the completion of molecular bridges between plastics and erythrocytes.

The first centrifuging speed $V_1$ is maintained for sufficient time to build and complete the molecular bridges, if any, between plastic and erythrocytes. The bridges are made up of the following chain of bonds:

Plastic+IgG 23/antiglobulin 27/IgG 25/positive erythrocytes 24.

In practice, the reaction is brought about in a cup having a cone aperture angle of 120°, and the first centrifuging stage is carried out at an acceleration of approx. 200 g for about 1 minute.

Figure 14B:
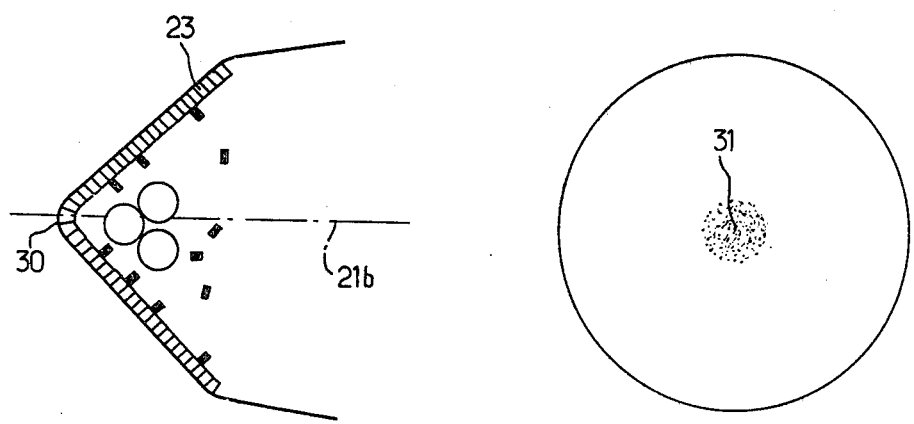

(e) This is followed by a second centrifuging step at a speed $V_2$ greater than $V_1$. The second stage is used to show the difference between a positive and a negative reaction. The speed $V_2$ is chosen so that the resulting centrifugal force drives negative erythrocytes, if any, to the cup apex 30 and collect them there (FIG. 14b) but does not drive the positive erythrocytes, since they are still attached to the cup wall by the IgG 23, the anti-human IgG molecules 27 and the IgG 25 (FIG. 14a). Speed $V_2$ is therefore chosen so that the detachment force $F_{d2}$ produced by centrifuging is greater than the sum of the non-specific bonding forces FNS holding a negative erythrocyte to the cup bottom but less than the sum of the non-specific bonding forces and the specific bonding forces (i.e. FNS+FS) holding a positive erythrocyte to the cup bottom.

In practice, when the reaction is brought about in a cup having an apex angle of 120°, the second centrifuging operation is carried out at an acceleration of approx. 1600 g for a time from a few seconds to a few tens of seconds.

The results of analysis are clear immediately after the reaction.

Thus, in the case of a positive reaction, i.e. in the case where the analysed erythrocytes do in fact have antigen D activity, all the erythrocyte/IgG complexes 26 remain stuck to the bottom of the cup by the human anti-IgG molecules 27 (FIG. 14a) and the human IgG 23. In that case, if the cup is examined along its axis 21b (the right part of FIG. 14a) a uniform mono-layer of erythrocytes can be seen over the entire bottom surface of the cup—i.e. adhesion occurs.

If, on the other hand, the analysed erythrocytes do not have antigen D activity, they are driven during the second centrifuging stage towards the cup apex 30 and collect there. If the cup is examined along its axis, the formation of a "micro-deposit" 31, consisting of erythrocytes, is observed (right part of FIG. 14b). No adhesion occurs.

The amounts of reagents used are not critical. For example, in a cup having a diameter between 1 and 7 mm, the volume of liquid introduced is between 15 and 250 µl. Advantageously equal volumes of erythrocyte suspension and antiglobulin are introduced.

The method has been described in its application to the search for D antigen radicals on erythrocytes, but it can be used under the same conditions to find whether the serum or plasma of a human blood sample contains the specific "anti-D" antibody. In that case, the serum to be analysed is incubated with test erythrocytes known to have the specific "D" antigenic activity. If the serum being analysed contains the specific anti-D antibody, the specific anti-D antibody immunoglobulins supplied by the serum become fixed to the D antigen radicals on the erythrocytes.

Next, the thus-incubated erythrocytes are washed and placed in the vessel simultaneously with the anti-globulin, as previously described, followed by the previously-mentioned centrifuging steps.

If the reaction is positive, i.e. if the serum under analysis does in fact contain the specific anti-D antibody, a uniform mono-layer of erythrocytes form and stick to the bottom surface of the cup, owing to the formation of molecular bridges between the plastics+IgG/anti-IgG/IgG and the erythrocytes. On the other hand, if the serum under analysis does not contain the specific anti-D antibody, the reaction is negative and the erythrocytes, which have not been able to stick to the bottom of the cup, collect in a micro-deposit at the cup apex at the end of the reaction.

The method has previously been described in reference to the search for D-antigen radicals carried by erythrocytes or for specific anti-D antibodies contained in blood serum or plasma, but it can also be used to detect any other erythrocyte antigen or any other antibody in blood plasma. In the case where a search is made for a particular erythrocyte antigen, and it is desired to find out whether certain erythrocytes actually have the antigen activity, the erythrocytes are incubated with a test serum containing the known antibody specific to the sought-after antigen. Contrariwise, if we wish to know whether blood plasma contains a particular antibody, the serum is incubated with test erythrocytes known to have the antigen activity corresponding to the sought-after antibody.

The test erythrocytes can bear antigen radicals specific to the sought-after antibody. Alternatively the test erythrocytes may be cells of a different nature or suitable particle, e.g. plastics particles or cells or particles on to which antigen radicals specific to the sought-after antibody have been fixed.

This is followed by the various subsequent steps as previously mentioned, modifying the various operating parameters if required, e.g. those defining centrifuging, so as to show whether adhesion occurs or not.

This second example of the method according to the invention may also be used to detect any kind of cell antigen, e.g. the antigen carried by lymphocytes, or platelet-forming antigens, if a suitable choice is made of reagents, i.e. the test serum, the immunoglobulins to be fixed to the bottom of the cup, and the antiglobulin.

This second example of the method according to the invention can be embodied in a variant which will now be described. As in the previous example, it is desired to determine whether the erythrocytes in a human blood sample have or do not have D-antigen activity.

(a) As in the previously described variant, the first step consists in preparing the conical bottom of the plastic cup so that it becomes coated with human IgG, i.e. immunoglobulins from the same animal species and in the same immunochemical class as in the specific D-antigen antibody used in the next step.

(b) Next, as before, the erythrocytes to be analysed are immersed in a suitable physiological solution in a vessel other than the cup and incubated with a test serum containing the known specific anti-D antibody (the anti-D test serum). After being incubated with the test serum, the erythrocytes are advantageously washed in physiological solution.

(c) Next, the thus-treated erythrocytes are incubated outside the cup with an antiglobulin, i.e. an animal immune serum supplying human anti-IgG immunoglobulins. This incubation is brought about under normal temperature conditions, e.g. at 20° C. and for sufficient time to ensure that the maximum proportion, or at least a high percentage, of IgG molecules fixed to the erythrocytes (if positive) react with anti-human IgG molecules which adhere thereto. Advantageously, the incubation is continued for 20 minutes.

The anti-globulin used is advantageously in high concentration, for the same reasons as previously given. In the present case, the antiglobulin used has a strength of at least 128 in the Coombs technique and is only slightly diluted, if at all (dilution ratio $\frac{1}{2}$ or $\frac{1}{4}$).

(d) At the end of this incubation period, the reaction medium comprising the suspension of erythrocytes and antiglobulin is transferred to the cup, the bottom of which is coated with human IgG.

(e) This is immediately followed by the first centrifuging step, by rotating the cup around an axis perpendicular to its axis of revolution. Centrifuging is performed at a speed $V_1$ sufficient to press the erythrocytes against the cup bottom but insufficient to destroy the non-specific bonding forces holding both the negative and the positive erythrocytes against the cup wall. Speed $V_1$ is therefore such that the resulting detachment force is less than the sum of the non-specific bonding forces FNS. Speed $V_1$ is kept up for sufficient time to form molecular chains consisting of a human IgG fixed to the cup bottom, a anti-human IgG molecule and a human IgG specifically fixed to a D-antigen radical of an erythrocyte. The time is chosen in accordance with the nature of the antigen or the antibody to be detected. In the present case, centrifuging is performed at an acceleration of about 200 g for about a minute.

(f) This is followed by a second centrifuging operation, as in the first embodiment.

More specifically, the centrifuging speed is increased to a value $V_2$ such that, as already explained, the resulting detachment force is sufficient to drive to the cup apex those erythrocytes which have not been bonded to the cup except by non-specific forces, i.e. negative erythrocytes, but is not sufficient to drive erythrocytes bearing the D-antigen radical, i.e. is not sufficient to break the sum of the non-specific bonding forces FNS and the specific bonding forces FS retaining positive erythrocytes on the sloping surface of the cup, by means of completed molecular bridges consisting of plastic+human IgG/anti-human IgG/anti-D human IgG/D-antigen of an erythrocyte.

The results observed are the same as before; if the reaction is positive, adhesion occurs and a uniform mono-layer of erythrocytes distributed on the cup bottom can be observed along the cup axis of revolution. On the other hand if the reaction is negative, no adhesion occurs and a micro-deposit is observed at the cup apex.

The main difference between the second embodiment and the previously-described embodiment is that anti-globulin incubation, i.e. the incubation of anti-human IgG molecules with erythrocytes previously incubated with the test serum, is not performed in the cup coated with human IgG immediately before the first centrifuging step but is performed outside the cup, and the reaction medium obtained after incubation is then introduced into the cup in order to be centrifuged. In the present case, the object is to obtain maximum asymmetry between the percentage of anti-human IgG molecules reacting with the human IgG molecules fixed to the plastic and the percentage of anti-human IgG molecules reacting with the human IgG molecules fixed to the erythrocytes. Ideal conditions occur when the percentage of human IgG molecules fixed to the plastic and occupied by anti-human IgG molecules is equal to 0% and the percentage of human IgG molecules fixed to the erythrocytes and occupied by anti-human IgG molecules is the maximum, provided of course that the maximum is lower than the value which would result in direct agglutination of erythrocytes with one another via anti-human IgG molecules.

The reason is that the maximum sensitivity of the adhesion reaction is probably reached when maximum asymmetry of the distribution of the anti-IgG molecules bonded to each of the end links, i.e. to the IgG fixed to the plastic and to the IgG fixed to the erythrocytes, is obtained when the erythrocytes are first laid under pressure on the bottom surface of the cup, i.e. at the beginning of the first centrifuging step. The asymmetry should be such that the end link having the lower surface density of IgG fixes the larger percentage of anti-IgG molecules. In our present example, the end link having the lower surface density of IgG is the erythrocyte, since the plastic has a higher IgG surface density since the immunoglobulins have been fixed thereto to saturation.

Antiglobulin incubation of this kind is called "asymmetrical", whereas antiglobulin incubation in the first embodiment is called "symmetrical" since each of the IgG end links is placed in contact with the antiglobulin at the same moment.

In the case where erythrocyte or cell antigens or antibody are identified, asymetrical antiglobulin incubation brought about outside the cup in which the immuno-adhesion reaction occurs results in 10 to 100 times the sensitivity obtained with symmetrical antiglobulin incubation.

Consequently the second embodiment involving asymmetrical antiglobulin incubation is preferably used, inter alia in reactions which may be described as difficult, i.e. those in which a very small number of Ig immunoglobulins, e.g. IgG, are fixed to the erythrocytes, possibly because there is a very small quantity of the particular antibody to be identified in the analysed serum, or the cell antigen has a very low surface density on the analysed erythrocytes.

The method involving asymmetrical antiglobulin incubation can also be used to find whether a serum contains specifically anti-D antibody, in which case the serum being analysed is incubated with test erythrocytes known to have "D" antigen activity, and this is followed by the previously-mentioned operations.

The method can also be used for identifying erythrocyte antigens other than D antigen, or in general for identifying all kinds of cellular antigens such as lymphocyte or platelet-forming antigens, in which case the centrifuging parameters and the reagents used in the immuno-adhesion reactions will be suitably adapted to the serological system under analysis. Similarly, the method can be used to identify any kind of antibody in blood plasma or serum.

In the aforementioned example of the method according to the invention used for identifying erythrocyte or cell antigens or antibodies in blood plasma, the centrifuging for showing adhesion or non-adhesion is in two steps, the second step being at a higher speed than the first.

Alternatively, centrifuging can be at a single acceleration sufficient for all the corpuscles, e.g. the erythrocytes, to be at least temporarily stuck to the bottom wall of the vessel, the acceleration being such that the only corpuscles which are slowly and progressively torn from the wall and collected at the vessel apex are those, if any, which cannot adhere to the bottom wall owing to the impossibility of forming molecular chains made up of an immunoglobulin fixed to the plastics, an antiglobulin molecule and an immunoglobulin fixed to a corpuscle. In such cases, the acceleration during the single centrifuging step is kept slightly above the value corresponding to the average for breaking the specific bonding forces connecting both the negative-reaction and the positive-reaction corpuscles. The non-specific bonding forces are the only forces which hold the negative-reaction corpuscles. Since the acceleration or centrifuging speed is low, all the corpuscles will be pressed against the cup bottom for sufficient time for the molecular bridges, if any, to form, since the molecular bridges develop and are completed more quickly than the negative-reaction corpuscles are torn away. If the same centrifuging speed is kept up sufficiently long, all those corpuscles, if any, which have not been able to stick to the bottom of the cup owing to the impossibility of forming molecular bridges, will have been gradually torn from the cup bottom wall and collected at the apex, whereas the positive-reaction corpuscles will remain stuck to the bottom wall since those molecular bridges capable of forming will have done so.

In the case where the D-antigen activity of erythrocytes in a human blood sample is being detected, and when the analysis is performed in a cup having a cone apex angle of 120°, the single centrifuging step is brought about at an acceleration of about 250 g, and maintained at the same value for about 400 seconds.

Figure 16:
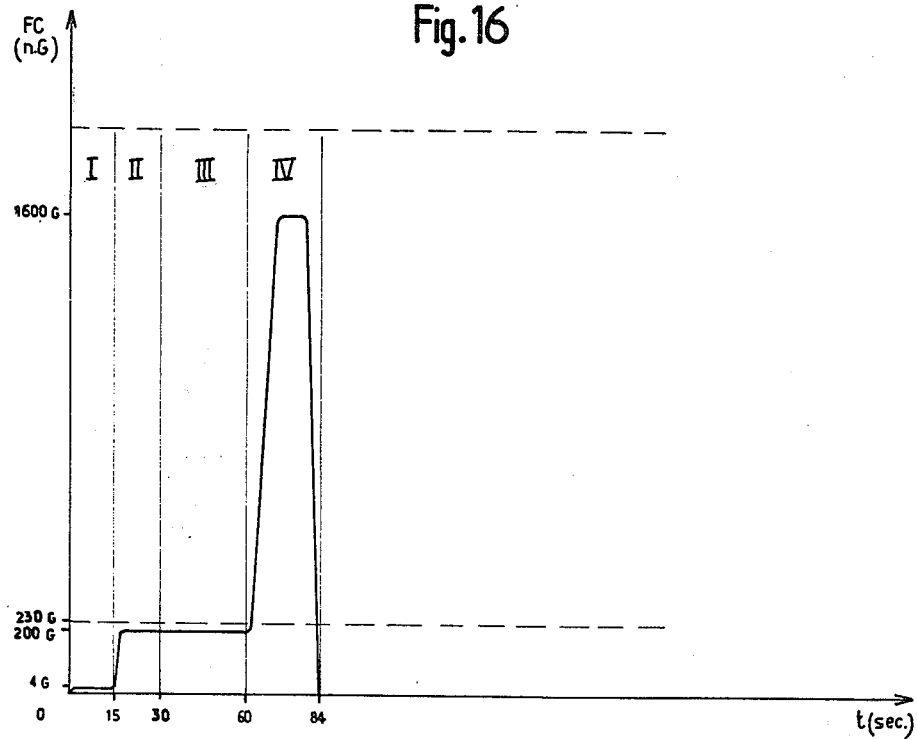
Figure 17:
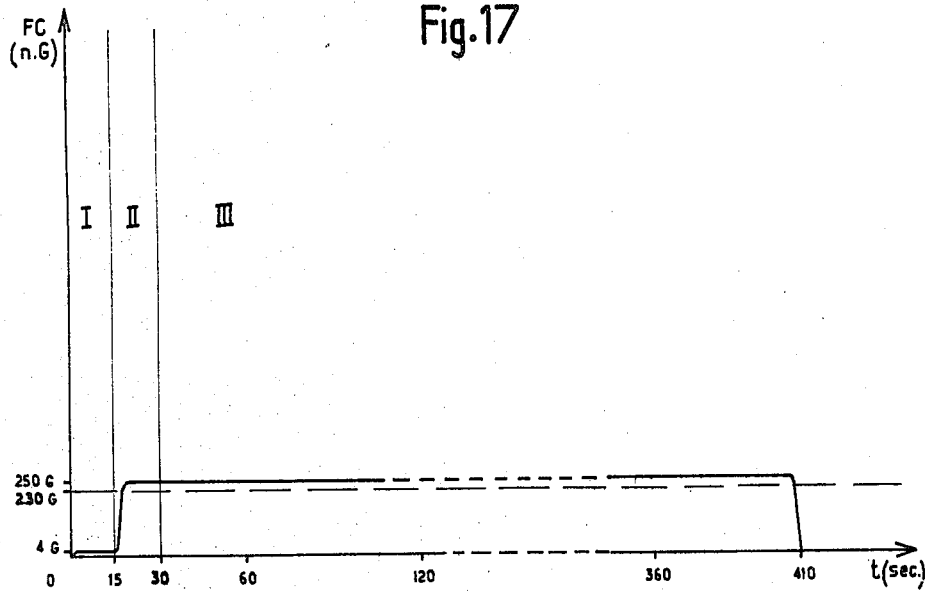
Figure 18:
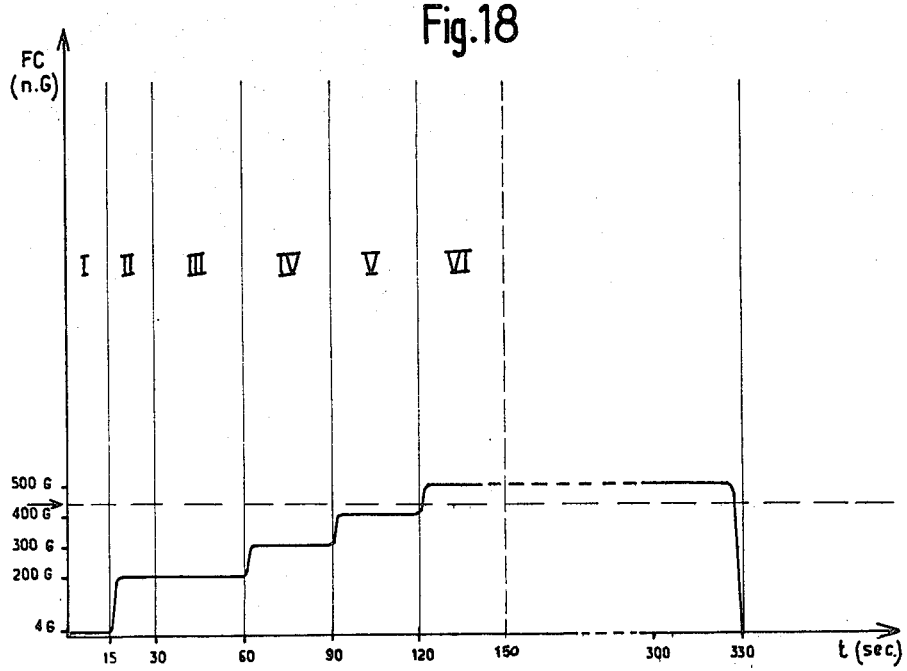

We shall now, with reference to FIGS. 16-18, describe three different centrifuging diagrams of use in reactions for identifying the aforementioned erythrocyte antigens or antibodies. In each diagram, the applied centrifugal force in g is shown on the ordinate and the centrifuging time in seconds is shown along the abscissa, the immuno-adhesion reaction being brought about in a cup having a conical bottom and an apex angle of 120°.

With reference to the first diagram (FIG. 16), corresponding to the case of symmetrical antiglobulin incubation, the cup is slightly accelerated at zero second (i.e. after the reaction medium containing the suspension of erythrocytes and antiglobulin has been introduced into the cup), and the cup is rotated around an axis parallel to its axis of revolution, the acceleration being 4 g in the present case. This phase I lasts from second 0 to second 15 and is an antiglobulin incubation step, since the speed is insufficient to rapidly move down the erythrocytes and lay them on to the bottom of the cup. If required, the reaction medium in the cup can be simultaneously agitated.

Next, the centrifuging acceleration is rapidly increased to a value below the average level for breaking the non-specific bonding forces FNS only. If this average level is estimated at 230 g (as in the present example where the object is to detect D-antigen activity on erythrocytes in a human blood sample) the centrifuging acceleration is raised to 200 g. During the step between the 15th and the 30th second, the erythrocytes move down towards the bottom of the cup and have all reached the bottom at second 30.

The centrifuging acceleration is kept at 200 g until the 60th second. During the resulting step III—i.e. from second 30 to second 60—the erythrocytes are laid under pressure on the cup bottom, during which time any molecular bridges capable of doing so can form between the plastics and the erythrocytes, so that practically all the molecular bridges are complete by the 60th second.

Next, the centrifuging acceleration is rapidly increased to a value sufficient to break all the non-specific bonding forces, the only forces which hold negative erythrocytes to the cup. Of course the acceleration must be below the value which will break the specific bonding forces combined with the non-specific bonding forces holding the positive erythrocytes against the plastics. In the present case, the acceleration is raised to 1600 g. Consequently during the last step (step IV), the non-specific bonding forces are broken in the case when they are the only forces holding the erythrocytes against the plastics. This step is associated by the rapid collecting of those erythrocytes which have been torn away. Centrifuging is finally stopped at second 84.

This centrifuging diagram, apart from a slight modification can be applied to the method in which asymmetrical antiglobulin incubation is brought about. In that case, step I (i.e. agitation and antiglobulin incubation in the cup) is eliminated since antiglobulin incubation is brought about outside the cup between the antiglobulin and the erythrocytes previously incubated with the test serum (or the serum to be analysed with the test erythrocytes). After asymmetrical antiglobulin incubation is complete, the reaction medium is transferred to the cup, followed immediately by the first centrifuging at an acceleration of 200 g.

A second kind of centrifuging which can be applied to reactions for identifying erythrocyte antigens or antibodies is represented by the diagram in FIG. 17.

As in the diagram in FIG. 16, centrifuging at very low acceleration (4 g in the present case) is applied until the 15th second, during a step I of symmetrical antiglobulin incubation, during which the cup is agitated if necessary.

At the 15th second, the centrifuging acceleration is rapidly increased, but in the present case to a value very slightly greater than that corresponding to the average level for breaking the non-specific bonding forces only. Since the average level is estimated at 230 g in the present case, the acceleration is raised to 250 g. Between the 15th and the 30th second the erythrocytes move down (step II) and all touch the bottom of the cup at second 30. Since the centrifuging acceleration is maintained at 250 g, i.e. slightly above the average level required to break the non-specific bonding forces, the falling phase II is immediately followed by a phase III during which the non-specific bonding forces are slowly and gently broken when they are the only forces holding an erythrocyte to the plastic and the erythrocyte belongs to the negative-reaction fraction having the smallest non-specific bonding forces. This step, therefore, is accompanied by a step during which the torn-away cells slowly and progressively collect. In the present case the collection rate is very low, in that immediately after the erythrocytes have moved down, they remain pressed against the bottom of the cup for sufficient time for molecular bridges to form when capable of doing so, since the molecular bridges develop more quickly than the cells are torn away. Thus, since the centrifuge acceleration is still kep at 250 g, all the molecular bridges capable of forming are complete after a certain time, whereas the erythrocytes which are not specifically bonded to the bottom of the cup continue to be gradually torn away. Phase III continues for a relatively long time and stops at e.g. the 410th second.

The method of tearing off applied in the present case is so gentle that the results are very sensitive. This is particularly suitable for reactions involving weak bonds between erythrocytes and the plastics.

The diagram in FIG. 18 corresponds to centrifuging controlled in response to the developing reactions. The process is brought about simultaneously in (a) a cup in which the reaction for analysing the sample occurs and (b) in a cup in which a negative control reaction occurs, the control cup being illuminated by a stroboscopic flash at each revolution of the centrifugation.

The method of control is similar to that explained hereinbefore with reference to the detection of $HB_s$ antigen. A magnified image of the bottom of the cup in the negative control reaction is filmed by a television camera and analysed, e.g. once per second, i.e. the surface and the opacity of the image of the micro-deposit forming in the negative control reaction is compared with the surface and opacity of the reference micro-deposit in a typical negative reaction brought about previously.

The diagram in FIG. 18 corresponds to a centrifuging program applied to a reaction for identifying erythrocyte or cell antigens or antibodies wherein the mean level for breaking the non-specific bonding forces alone corresponds to a centrifuge acceleration of 450 g. This controlled centrifuge diagram can in fact be applied to a serological system having characteristics, (inter alia the mean level for breaking the non-specific bonding forces) which are not known in advance.

As before, we shall assume that the process includes symmetrical antiglobulin incubation. In that case, the centrifuge acceleration up to second 15 is kept at 4 g, i.e. too low to draw down or rapidly press the corpuscles or cells against the bottom of the cup. This is the antiglobulin incubation step I, during which the cup is agitated if required.

At the 15th second, the centrifuge acceleration is rapidly increased to 200 g. Between the 15th and the 30th second, the cells or corpuscles rapidly move down to the bottom of the cup (step II). This is followed by step III, up to the 60th second, during which a coating of cells or corpuscles is formed on the bottom of the cup and all molecular bridges capable of doing so form between the bottom of the cup and the cells or corpuscles.

At the end of the coating step, i.e. at second 60, the acceleration is increased by 100 g, i.e. to 300 g for 30 seconds (step IV). At second 90, the surface and opacity of the micro-deposit in the negative control reaction is measured and compared with the micro-deposit in the typical reference negative reaction. If the measured surface and opacity of the control micro-deposit are less than the surface and opacity of the reference micro-deposit, this means that the acceleration of 300 g is too small to break the non-specific bonding forces.

Accordingly, the centrifuge acceleration is increased by a further 100 g, giving an acceleration of 400 g for 30 seconds (phase V). At second 120, the surface and opacity of the control micro-deposit are again measured and compared with the reference micro-deposit. In the present case, where the mean level for breaking the non-specific bonding forces is 450 g, the measured surface and opacity of the micro-deposit in the negative control reaction obtained after centrifuging at 400 g will still be below the corresponding measurements for the reference micro-deposit since, in the negative control reaction, the erythrocytes connected to the cup by the non-specific bonding forces cannot be torn away.

Accordingly, the centrifuge acceleration is increased by a further 100 g to 500 g (step VI). After 30 seconds, i.e. at second 150, the surface and opacity of the micro-deposit from the negative control reaction is again measured and compared with the corresponding measurements for the reference micro-deposit. In the present case, the mean level for breaking the non-specific bonding forces has been exceeded and consequently the micro-deposit obtained in the negative control reaction has a surface and opacity at least equal to the surface and opacity of the reference micro-deposit. Accordingly, second 120 begins the step when the non-specific bonding forces by themselves are broken and the torn-away erythrocytes are simultaneously collected. The centrifuge acceleration is kept at 500 g and centrifuging is finally stopped when the surface and opacity of the micro-deposit from the negative control reaction correspond to a quantity of detached erythrocytes which just represents a true relative reaction. In the present case, centrifuging is stopped at second 330.

The thresholds for distinguishing between a positive and a negative reaction are defined in the manner explained previously with reference to the methods for detecting $HB_s$ antigen.

Thus, if the percentage of erythrocytes collecting in a micro-deposit and indicating a true negative reaction is 12%, as determined by previous experiments, and if the standard deviation is evaluated at 3%, the descrimination threshold of a true negative reaction, as previously mentioned, corresponds to 18% erythrocytes collected in a micro-deposit, whereas the discrimination threshold of a positive reaction corresponds to 6% erythrocytes collected in a micro-deposit.

Finally, the method according to the invention can be used for quantitatively measuring the proportion of the particular erythrocyte antigen or cell antigen or the particular antibody which is to be detected. This is because the surface and/or opacity of the resulting micro-deposit is dependent on the amount of antigen and antibody present in the analysed medium. Consequently, after the surface and/or opacity of the micro-deposit formed in a positive reaction has been measured, the amount of antigen or antibody present in the medium can be determined simply by referring to the corresponding values obtained for a range of standard products or a previously-prepared calibration curve.

The second example of the method according to the invention can also be applied, in similar manner to the first and under the same centrifuging conditions, to samples in which it is required to identify erythrocyte antigens or cell antigens or antibodies having varying natures and specificity.

The reason, as explained hereinbefore, is that the possibility of detachment depends only on the slope of the bottom of the cup. Consequently, in each reaction in question, a choice will be made of the cup having the most appropriate slope for the reaction, the slope being such that only the negative-reaction cells or particles will be detached at the chosen acceleration.

I claim:

1. A method of analysing a biological medium to detect or identify virus antigens or erythrocyte or cell antigens or antibodies in the medium, the method involving immunological reactions between cells or particles, a serum and an antiglobulin, the reaction of analysis being conducted in a vessel the wall of which has a point of convergence or apex situated on the axis of symmetry of the vessel, wherein molecules of a reactant capable of immunologically reacting with the antiglobulin are fixed on the walls of the vessel, said antiglobulin being chosen for its capacity to immunologically and independently bind the cells or particles characterizing either positive or negative reaction with said molecules of reactant, then subjecting the reaction medium to a centrifugal force substantially parallel to said axis under conditions such that in a first period all the cells or particles, whether they characterize a reaction with a positive result or a negative result, progressively stick to and remain stuck to the wall of the vessel, the centrifugal force in said first period being such as to prevent a collection of said particles at the apex of the vessel, and then in a second period, only the cells or particles characterizing one kind of reaction remain stuck to the wall of the vessel whereas the cells or particles characterizing the other kind of reaction are collected at the apex of the vessel.

2. A method of analysing a biological medium to detect or identify virus antigens or erythrocyte or cell antigens or antibodies in the medium, the method involving immunological reactions between cells or particles and a serum and then between the thus-treated cells or particles and an antiglobulin, the reaction of analysis being conducted in a vessel the wall of which has a point of convergence or apex situated on an axis of symmetry of the vessel, wherein molecules of a reactant capable of immunologically reacting with the antiglobulin are fixed on the walls of the vessel, said antiglobulin being chosen for its capacity to immunologically and independently bind the cells or particles showing a positive reaction with said molecules of reactant, the reaction medium containing the treated cells or particles and the antiglobulin is introduced into the vessel and is subjected to a centrifugal force substantially parallel to the aforementioned axis under conditions such that at least the cells or particles showing a positive reaction, progressively stick to and remain immunologically stuck to the vessel wall by bonding forces of a first kind, i.e. immunological bonding forces involving the antiglobulin, which are added to bonding forces of a second kind, whereupon the last-mentioned cells are collected at the apex of the vessel by applying a centrifugal force sufficiently strong to destroy the bonding forces of the second kind but not sufficient to destroy the sum of the bonding forces of the first kind and the bonding forces of the second kind.

3. A method according to claim 2 for detecting or identifying virus antigens in blood plasma wherein Ig immunoglobulins in the immunochemical class X and from an animal species I are fixed on the wall of a vessel which has a point of convergence on an axis of symmetry of the vessel; a sample of the blood plasma to be analysed is incubated outside the vessel with a suspension of cells or particles onto which IgX I have already been fixed, after being chosen in accordance with the antibody specificity of the immunoglobulins towards the virus antigen to be detected; a reaction medium containing the thus-incubated suspension of cells or particles and a preferably concentrated antiglobulin (i.e.

a solution of molecules coming from an animal species II different from species I and presenting an antibody activity against IgX I, said molecules being called anti-IgX I) is subjected in the vessel to a centrifugal force parallel to said axis under conditions for bonding anti-IgX I molecules and IgX I molecules and thus forming molecular bridges between the wall of the vessel and the cells or particles via anti-IgX I molecules; centrifuging is carried out at a first acceleration for sticking all the cells to the wall of the vessel, and is then suddenly stopped so that the cells or particles showing a negative reaction can come loose, after which centrifuging is continued at a second acceleration for collecting at the apex of the vessel those cells or particles, if any, which could not adhere to the vessel wall because of the breaking of the molecular bridges formed by the anti-IgX I molecules.

4. A method according to claim 3, wherein centrifuging is stopped for a time sufficient to obtain, in the case of a reaction with a negative result, saturation by anti-IgX I molecules of the IgX I molecules fixed on the facing surfaces of the cells or particles on the one hand, and of the vessel walls on the other hand.

5. A method according to claim 3, wherein the suspension of cells or particles is washed with physiological solution after being incubated outside the vessel with the blood plasma to be analysed.

6. A method according to claim 3, wherein the solution of anti-IgX I molecules used has a strength of at least 128 in the Coombs method, and is pure or diluted in a ratio of ½ or ¼.

7. A method according to claim 3, wherein the suspension of cells or particles previously incubated with the blood plasma for analysis is introduced into the vessel simultaneously with the solution of anti-IgX I molecules.

8. A method according to claim 3, wherein the suspension of cells or particles previously incubated with the biological medium to be analysed is first introduced into the vessel, followed by the solution of anti-IgX I molecules.

9. A method according to claim 3, wherein, before the first centrifuging phase, the components of the reaction medium, i.e. the solution of anti-IgX I molecules and the suspension of cells or particles already incubated with the sample, are incubated for a time at most equal to the one for which 10% of the IgX I molecules fixed on to the cells or particles or on to the vessel wall have reacted with the anti-IgX I molecules.

10. A method according to claim 9, wherein the reaction medium is agitated during the incubation.

11. A method according to claim 9, wherein the duration of incubation is comprised between a few seconds and a few tens of seconds.

12. A method according to claim 3, wherein the acceleration and the duration of each centrifuging step, i.e. the first step, the subsequent stoppage and the second step, are determined in advance and correspond to the ones giving the best results in a preliminary test using the reactants under the same conditions and with a reference negative reaction—i.e. so that practically 100% of the cells or particles adhere to the vessel wall at the end of the first centrifuging step, the IgX molecules fixed to the vessel wall and to the facing surfaces of the cells or particles are sufficiently saturated with anti-IgX I molecules at the end of the stop phase for the cells to come loose from the vessel wall, and the cells are torn loose and collected at the apex of the vessel during the second centrifuging step.

13. A method according to claim 12, wherein the moment when the second centrifuging step is stopped is automatically determined, since the process is carried out simultaneously (a) in a vessel in which the sample-analysis reaction is carried out and (b) in a vessel in which a negative control reaction is carried out, the image of the bottom of the control vessel being recorded and analysed at regular intervals during the second centrifuging step, which is finally stopped when the image of the bottom of the control vessel corresponds to at least approx. 18% cells or particles collected at the apex of the vessel.

14. A method according to claim 3, used for searching for $HB_s$ virus antigen in a human blood sample.

15. A method according to claim 14, wherein analysis is carried out in a vessel having a conical bottom and an apex angle of 120°, the first centrifuging step is performed at an acceleration of 200 g between the 15th and the 60th second after introduction into the vessel of the reaction medium containing the solution of anti-IgX I molecules and the suspension of cells or particles previously incubated with the sample for analysis, centrifuging is stopped between the 60th and the 300th second after introduction of the reaction medium into the vessel, and the final centrifuging step is carried out at 500 g acceleration for 40 seconds.

16. A method according to claim 2 for detecting or identifying cell antigens (or anticell antibodies) in blood, wherein immunoglobulins in the immunochemical class X and from an animal species I (called IgX I) are fixed on the wall of a vessel, which has a point of convergence on an axis of symmetry of the vessel; a suspension of blood globules under analysis is incubated with a test serum (or the blood plasma to be analysed is incubated with a suspension of test globules) under conditions for fixing IgX I on the globules; and a reaction medium comprising the suspension of thus-incubated globules and a preferably concentrated antiglobulin (i.e. a solution of molecules coming from an animal species II different from species I and presenting an antibody activity against IgX I, the molecules being called anti-IgX I) is subjected in the vessel to a centrifugal force parallel to the axis of symmetry of the vessel under conditions such that any anti-IgX I molecules can become bonded with IgX I and thus molecular bridges can be formed between the globules and the vessel wall via anti-IgX I molecules, centrifuging being carried out so that the globules remain temporarily pressed on to the vessel wall so that the molecular bridges can form, and that the only globules which collect at the apex of the vessel are those, if any, which cannot adhere to the vessel wall due to the impossibility for molecular bridges via anti-IgX I molecules to be formed.

17. A method according to claim 16, wherein the suspension of globules for analysis (or the suspension of test globules) after being incubated outside the vessel with a test serum (or with the blood plasma to be analysed) is washed with physiological solution.

18. A method according to claim 16, wherein use is made of a solution of anti-IgX I molecules having a strength of at least 128 in the Coombs method, either pure or diluted in a ratio of ½ or ¼.

19. A method according to claim 16, wherein the two components of the reaction medium, i.e. the suspension of globules and the solution of anti-IgX I molecules, are introduced separately and simultaneously into the vessel.

20. A method according to claim 16, wherein the suspension of previously-incubated globules is introduced into the vessel before the solution of anti-IgX I molecules.

21. A method according to claim 19 or claim 20, wherein before centrifuging, the two components of the reaction medium, i.e. the suspension of previously incubated globules and the solution of anti-IgX I molecules, are incubated in the vessel for a time at most equal to the one for which 10% of the IgX I molecules fixed on the globules or on the vessel wall have reacted with the anti-IgX I molecules.

22. A method according to claim 21, wherein the reaction medium is agitated during the incubation.

23. A method according to claim 21, wherein the duration of the incubation is comprised between a few seconds and a few tens of seconds.

24. A method according to claim 16, wherein the reaction medium is not introduced into the vessel and centrifuged until after the suspension of globules has been incubated outside the vessel with the solution of anti-IgX I molecules, centrifuging being performed immediately after the reaction medium has been introduced into the vessel.

25. A method according to claim 24, wherein the suspension of globules and the solution of anti-IgX I molecules are incubated for about 20 minutes.

26. A method according to claim 16, wherein centrifuging is carried out at two different accelerations, i.e. a first acceleration such that all the globules are pressed against the vessel wall and a second and higher acceleration such that only those globules which cannot adhere to the vessel wall collect at the vessel apex.

27. A method according to claim 16, wherein centrifuging is performed at a single acceleration for at least temporarily pressing all the globules against the vessel wall, said acceleration being such that only those globules, if any, which cannot stick to the wall of the vessel are slowly and gradually detached from the wall and collect at the vessel apex.

28. A method according to claim 26 or claim 27, wherein, in order to automatically determine the time for finally stopping the centrifuging, the method is carried out simultaneously and under the same conditions (a) in a vessel in which the sample is being analysed and (b) in a vessel in which a negative control reaction is being brought about; the micro-deposit formed in the negative control reaction is recorded and analysed at regular intervals, and centrifuging is finally stopped when analysis of the micro-deposit from the negative control reaction indicates that approximately 18% of the globules have collected at the vessel apex.

29. A method according to claim 16, wherein centrifuging is servo-controlled in accordance with the progress of the reactions, the method being performed simultaneously and under the same conditions (a) in a vessel in which the sample is being analysed and (b) in a vessel in which a negative control reaction is being brought about; the image of the micro-deposit being formed in the negative control reaction is recorded and analysed at regular intervals, the increase curve of the micro-deposit is compared with that of the micro-deposit from a negative reference reaction, and the centrifuging speeds and times are controlled so that the increase curve of the micro-deposit under analysis corresponds to the reference increase curve.

30. A method according to claim 29, wherein centrifuging is finally stopped when analysis of the micro-deposit from the negative control reaction indicates that at least approx. 18% of the globules have collected at the vessel apex.

31. A method according to claim 29, wherein the analysis reaction is performed in a vessel having a conical bottom and an apex angle of 120°, and after the suspension of globules has been incubated with the solution of anti-IgX I molecules, the vessel containing the reaction medium is rotated around an axis perpendicular to the cone axis at an acceleration less than that at which the globules showing a negative reaction are torn away free the bottom wall of the vessel, the acceleration being continued for 45 seconds, after which the acceleration is progressively increased by 100 g every 30 seconds and the micro-deposit formed in the negative control reaction at the end of each 30 second period is analysed until the analysis shows that the percentage of globules which have collected at the vessel apex is at least equal to that obtained in the negative reference reaction.

32. A method according to claim 26, wherein the analysis reaction is brought about in a vessel having a conical bottom and an apex angle of 120°, and after the suspension of globules has been incubated with the solution of anti-IgX I molecules, centrifuging is brought about by rotating the vessel around an axis perpendicular to the axis of its conical bottom at an acceleration of 200 g for 45 seconds, after which the acceleration of centrifuging is rapidly increased to 1600 g, centrifuging being finally stopped at the instant when, in a control negative reaction under the same conditions, the percentage of globules collected at the vessel apex is at least equal to the percentage defining the discrimination threshold of a negative reaction.

33. A method according to claim 27, wherein the analysis reaction is performed in a vessel having a conical bottom and an apex angle of 120°, and after the suspension of globules has been incubated with the solution of anti-IgX I molecules, centrifuging is brought about by rotating the vessel around an axis perpendicular to the axis of its conical bottom and at an acceleration of 250 g, and centrifuging is stopped at the instant corresponding to the time when, in a negative control reaction under the same conditions, the percentage of globules collecting at the apex of the vessel is at least equal to the percentage defining the discrimination threshold of a negative reaction.

* * * * *